US011202576B2

(12) United States Patent
Seo et al.

(10) Patent No.: US 11,202,576 B2
(45) Date of Patent: Dec. 21, 2021

(54) METHOD FOR OBTAINING HEART RATE AND ELECTRONIC DEVICE FOR THE SAME

(71) Applicant: Samsung Electronics Co., Ltd., Gyeonggi-do (KR)

(72) Inventors: Yunhwa Seo, Gyeonggi-do (KR); Sun-Young Park, Gyeonggi-do (KR); Byungjun Lee, Gyeonggi-do (KR); Jeong Gwan Kang, Gyeonggi-do (KR); Seung Hyuck Shin, Gyeonggi-do (KR); Taeho Kim, Chungcheongbuk-do (KR); Jeong-Min Park, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 834 days.

(21) Appl. No.: 15/797,136

(22) Filed: Oct. 30, 2017

(65) Prior Publication Data

US 2018/0140204 A1 May 24, 2018

(30) Foreign Application Priority Data

Nov. 23, 2016 (KR) .................. 10-2016-0156251

(51) Int. Cl.
*A61B 5/0205* (2006.01)
*A61B 5/024* (2006.01)
(Continued)

(52) U.S. Cl.
CPC ........ *A61B 5/0205* (2013.01); *A61B 5/02416* (2013.01); *A61B 5/02438* (2013.01);
(Continued)

(58) Field of Classification Search
CPC .............. A61B 5/0205; A61B 5/02416; A61B 5/02438; A61B 5/721; A61B 5/1118; A61B 5/1123
See application file for complete search history.

(56) References Cited

U.S. PATENT DOCUMENTS 9,456,787 B2   10/2016  Venkatraman et al.
2014/0288436 A1*   9/2014  Venkatraman ......... A61B 5/742
                                                                    600/479
(Continued)

FOREIGN PATENT DOCUMENTS

CN          104207756 A       12/2014

OTHER PUBLICATIONS

European Search Report dated May 4, 2018.
European Search Report dated Apr. 30, 2021.
Chinese Office Action: dated Jul. 20, 2021.

*Primary Examiner* — Carrie R Dorna
(74) *Attorney, Agent, or Firm* — Cha & Reiter, LLC

(57) ABSTRACT

An electronic device and a method are provided. The electronic device can include a motion sensor, a heart rate monitor sensor, and a processor functionally coupled with the motion sensor and the heart rate monitor sensor. The processor can be configured to obtain first motion sensor data for a first duration using the motion sensor, obtain first heartbeat data for the first duration using the heart rate monitor sensor, determine an exercise type based on the first motion sensor data, determine a heartbeat prediction range based on at least one of the first motion sensor data, the exercise type, and the first heartbeat data, obtain second heartbeat data for a second duration using the heart rate monitor sensor, determine whether the second heartbeat data falls within the heartbeat prediction range, and determine heartbeat data of the second duration based on the determination result.

19 Claims, 14 Drawing Sheets

(51) Int. Cl.
  *A61B 5/11* (2006.01)
  *G16H 20/30* (2018.01)
  *G16H 40/60* (2018.01)
  *A61B 5/00* (2006.01)
  *A61B 5/0245* (2006.01)

(52) U.S. Cl.
  CPC ........... *A61B 5/1118* (2013.01); *A61B 5/1123* (2013.01); *A61B 5/721* (2013.01); *G16H 20/30* (2018.01); *G16H 40/60* (2018.01); *A61B 5/0245* (2013.01); *A61B 5/6802* (2013.01); *A61B 5/6823* (2013.01); *A61B 5/6831* (2013.01); *A61B 2503/10* (2013.01); *A61B 2560/0242* (2013.01)

(56) References Cited

U.S. PATENT DOCUMENTS

| | | | |
|---|---|---|---|
| 2015/0342479 A1 | 12/2015 | Liu et al. | |
| 2015/0374240 A1* | 12/2015 | Lee | A61B 5/4866 600/483 |
| 2016/0051157 A1 | 2/2016 | Waydo | |
| 2016/0051158 A1 | 2/2016 | Silva | |
| 2016/0051201 A1 | 2/2016 | Maani et al. | |
| 2016/0081627 A1* | 3/2016 | McGloin | A61B 5/1123 600/301 |
| 2016/0144235 A1 | 5/2016 | Martikka et al. | |
| 2018/0056126 A1* | 3/2018 | Eastman | A61B 5/1118 |

* cited by examiner

METHOD FOR OBTAINING HEART RATE AND ELECTRONIC DEVICE FOR THE SAME

CLAIM OF PRIORITY

This application claims priority under 35 U.S.C. § 119(a) to Korean Patent Application Serial No. 10-2016-0156251, which was filed in the Korean Intellectual Property Office on Nov. 23, 2016, the content of which is incorporated herein by reference.

TECHNICAL FIELD

The present disclosure relates generally to a method and an apparatus for obtaining a heart rate.

BACKGROUND

In recent, with advances in digital technology, various electronic devices such as a mobile communication terminal, a Personal Digital Assistant (PDA), an electronic notebook, a smart phone, a tablet Personal Computer (PC), and a wearable device are widely used. To support and expand functions, hardware and/or software of the electronic device steadily improve. For example, the electronic device can include one or more sensors and collect its state or user's biometric information using sensor data obtained from the sensor.

For example, the electronic device can measure a user's heart rate using a heart rate monitoring sensor. The heart rate monitoring sensor can include a light emitter and a light receiver, which may be optical sensors (e.g., green/red Light Emitting Diode (LED)). When the electronic device is attached to a user's body, the light emitter of the heart rate monitor can output light and the light receiver can receive the output light reflected from part of the user's body. By digitizing and arranging a quantity of the light received at the light receiver based on time, a signal indicating a particular frequency can be generated. The heart rate monitoring sensor can measure the heart rate by scanning a frequency corresponding to heartbeats from the generated signal.

For the accurate heart rate measurement, the user needs to wear the heart rate monitoring sensor on his/her chest. Also, when the heart rate monitoring sensor scans the frequency and the user moves, the frequency according to the movement may affect the frequency corresponding to the heartbeat. In this case, to measure the accurate heart rate, the frequency (e.g., noise) according to the movement needs to be removed from the signal generated by the heart rate monitoring sensor. In addition, when the heart rate monitoring sensor is not closely attached to the user's body part, the signal based on the quantity of the light received at the light receiver can be considerably unstable. As a result, an accurate heart rate may not be attained merely by removing various noises in the heart rate measurement.

SUMMARY

According to one aspect of the present disclosure, an electronic device can include a motion sensor, a heart rate monitor sensor, and a processor functionally coupled with the motion sensor and the heart rate monitor sensor. The processor can be configured to obtain first motion sensor data for a first duration using the motion sensor, to obtain first heartbeat data for the first duration using the heart rate monitor sensor, to determine an exercise type based on the first motion sensor data, to determine a heartbeat prediction range based on at least one of the first motion sensor data, the exercise type, and the first heartbeat data, to obtain second heartbeat data for a second duration using the heart rate monitor sensor, to determine whether the second heartbeat data falls within the heartbeat prediction range, and to determine heartbeat data of the second duration based on the determination result.

According to another aspect of the present disclosure, a method for operating an electronic device which includes a motion sensor and a heart rate monitor sensor, can include obtaining first motion sensor data for a first duration using the motion sensor, and obtaining first heartbeat data for the first duration using the heart rate monitor sensor, determining an exercise type based on the first motion sensor data, determining a heartbeat prediction range based on at least one of the first motion sensor data, the exercise type, and the first heartbeat data, determining whether second heartbeat data obtained for a second duration falls within the heartbeat prediction range, and determining heartbeat data of the second duration based on the determination result.

According to yet another aspect of the present disclosure, a computer-readable recording medium can include a program for obtaining first motion sensor data for a first duration using the motion sensor, and obtaining first heartbeat data for the first duration using the heart rate monitor sensor, determining an exercise type based on the first motion sensor data, determining a heartbeat prediction range based on at least one of the first motion sensor data, the exercise type, and the first heartbeat data, determining whether second heartbeat data obtained for a second duration falls within the heartbeat prediction range, and determining heartbeat data of the second duration based on the determination result.

According to various embodiments, using the user's exercise information and the sensor information, the heart rate measured by the heart rate monitor sensor can corrected and thus a more accurate heart rate can be attained.

According to various embodiments, the calories based on the heart rate can be calculated by acquiring the accurate heart rate through the heart rate correction.

According to various embodiments, by acquiring the accurate heart rate based on the user motion, various information can be provided using the heart rate.

Other aspects and salient features of the disclosure will become apparent to those skilled in the art from the following detailed description, which, taken in conjunction with the annexed drawings, discloses example embodiments of the disclosure.

BRIEF DESCRIPTION OF THE DRAWINGS

The above and other aspects, and features of certain example embodiments of the present disclosure will be more apparent from the following description taken in conjunction with the accompanying drawings, in which.

Throughout the drawings, like reference numerals will be understood to refer to like parts, components and structures.

DETAILED DESCRIPTION

Figure 1:
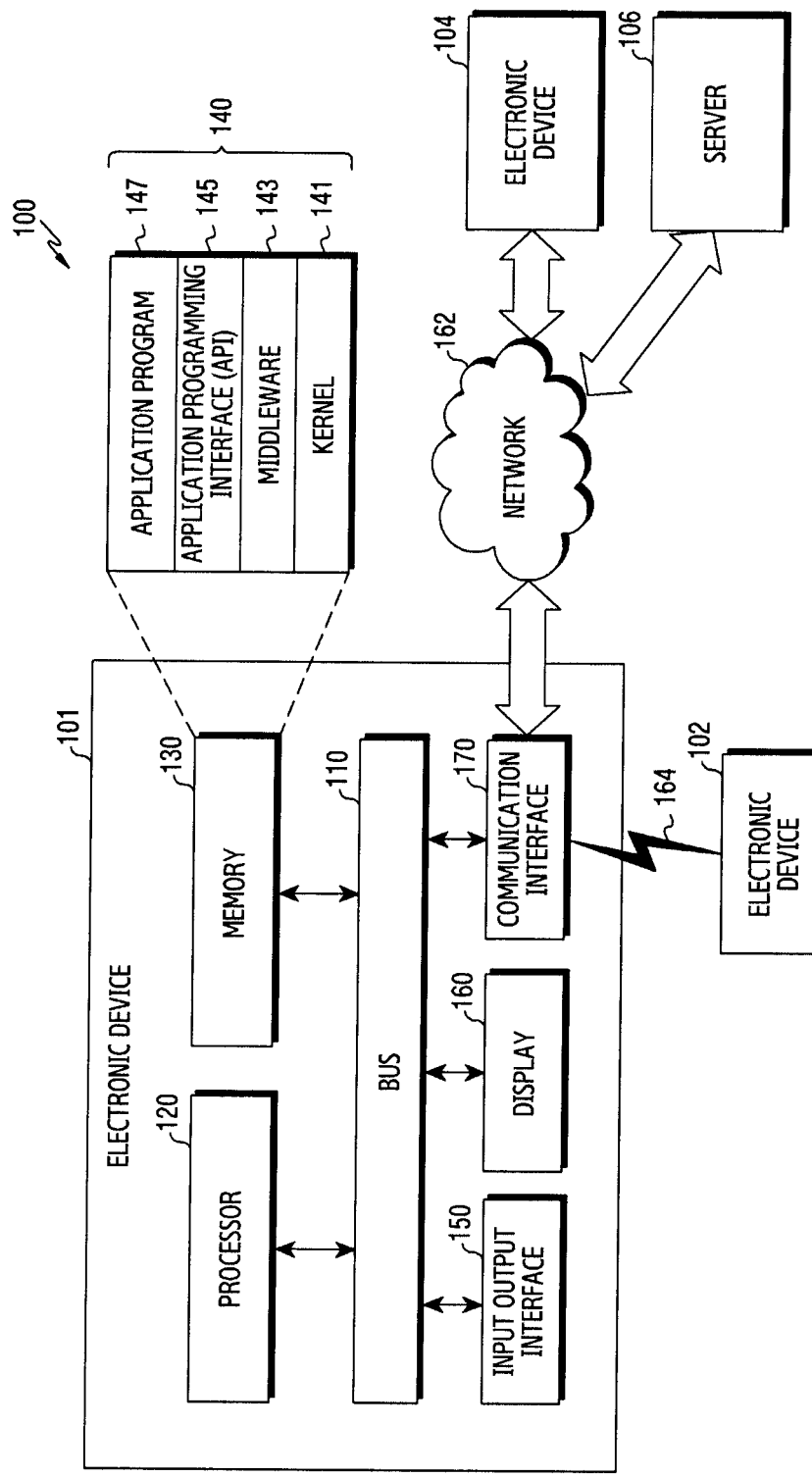
FIG. 1 is a block diagram of an electronic device in a network according to various embodiments.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements. As used herein, the expression "have", "may have", "include", or "may include" refers to the existence of a corresponding feature (e.g., numeral, function, operation, or constituent element such as component), and does not exclude one or more additional features. In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B. The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit), and therefore include straps, buckles, clasps, slings, locks or any other attachment which may secure the device to a user's body. According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology. Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments of the present disclosure.

An electronic device 101 within a network environment 100, according to various embodiments, will be described with reference to FIG. 1. The electronic device 101 may include a bus 110, a processor 120, a memory 130, an input/output interface 150, a display 160, and a communication interface 170. According to an embodiment of the present disclosure, the electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include one or more of a Central Processing Unit (CPU), an Application Processor (AP), and a Communication Processor (CP). The processor 120 may carry out, for example, calculation or data processing relating to control and/or communication of at least one other component of the electronic device 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data. Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150, for example, may function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a MicroElectroMechanical Systems (MEMS) display, and an electronic paper display. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106). The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short-range communication 164.

The short-range communication 164 may include at least one of, for example, Wi-Fi, Bluetooth, Near Field Communication (NFC), and Global Navigation Satellite System (GNSS). GNSS may include, for example, at least one of global positioning system (GPS), global navigation satellite system (Glonass), Beidou Navigation satellite system (Beidou) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS). The network 162 may include at least one of a telecommunication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. According to various embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

Figure 2:
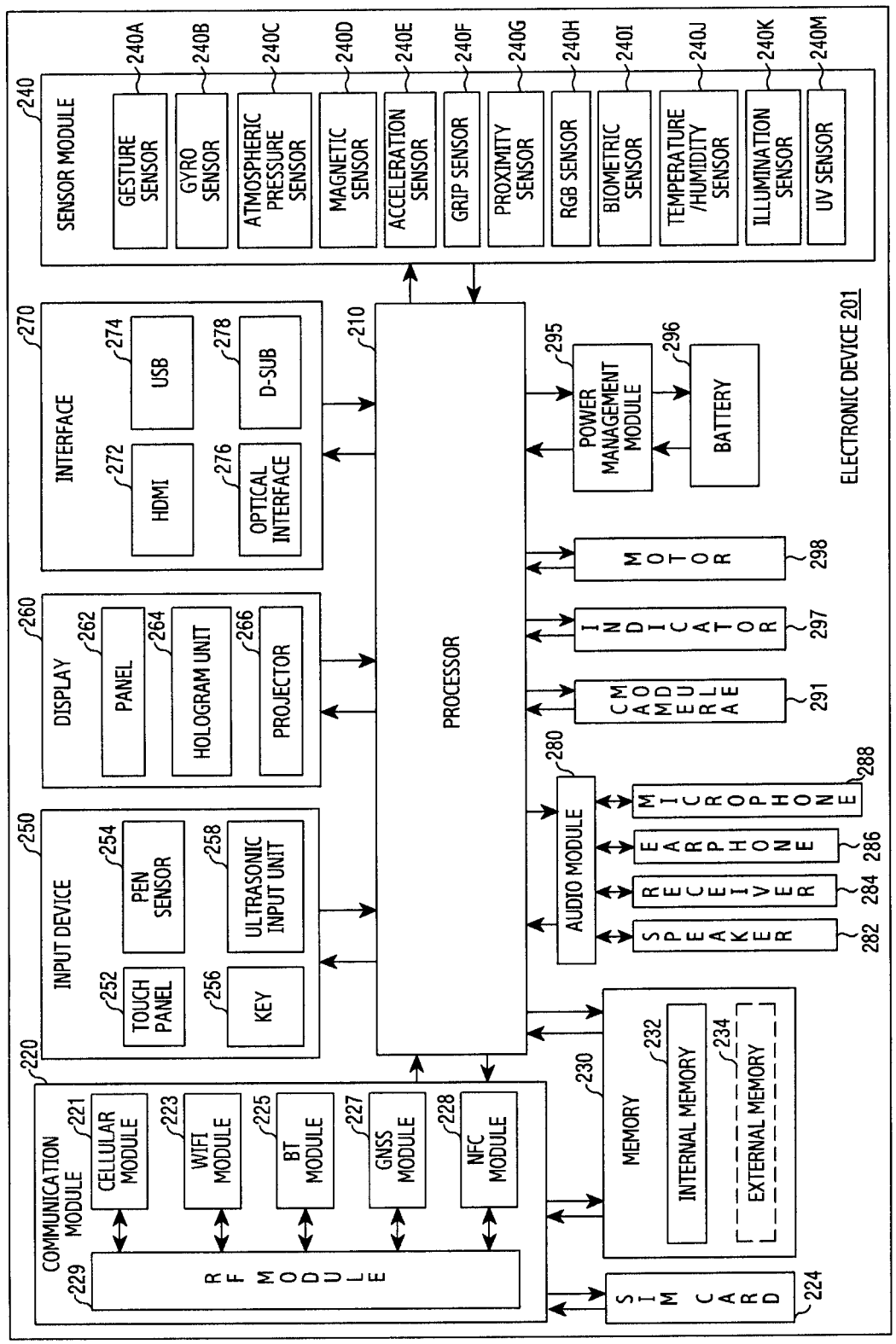
FIG. 2 is a block diagram of an electronic device according to various embodiments.

FIG. 2 is a block diagram of an electronic device according to various embodiments of the present disclosure.

The electronic device 201 may include, for example, all or a part of the electronic device 101 shown in FIG. 1. The electronic device 201 may include one or more processors 210 (e.g., Application Processors (AP)), a communication module 220, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include, for example, a cellular module 221, a Wi-Fi module 223, a BT module 225, a GNSS module 227 (e.g., a GPS or GNSS module 227, a Glonass module, a Beidou module, or a Galileo module), an NFC module 228, and a Radio Frequency (RF) module 229. The cellular module 221, for example, may provide a voice call, a video call, a text message service, or an Internet service through a communication network. According to an embodiment of the present disclosure, the cellular module 221 may distinguish and authenticate the electronic device 201 in a communication network using a subscriber identification module (e.g., SIM card) 224 (for example, the SIM card). According to an embodiment of the present disclosure, the cellular module 221 may perform at least some of the functions that the AP 210 may provide. According to an embodiment of the present disclosure, the cellular module 221 may include a communication processor (CP).

For example, each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one Integrated Chip (IC) or IC package. The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the wi-fi module 223, the BT module 225, the GNSS module 227, and the NFC module 228 may transmit/receive an RF signal through a separate RF module. The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like). The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMediaCard (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user. The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-sub-miniature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288. The camera module 291 is, for example, a device which may photograph a still image and a video. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or mediaFLO™.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
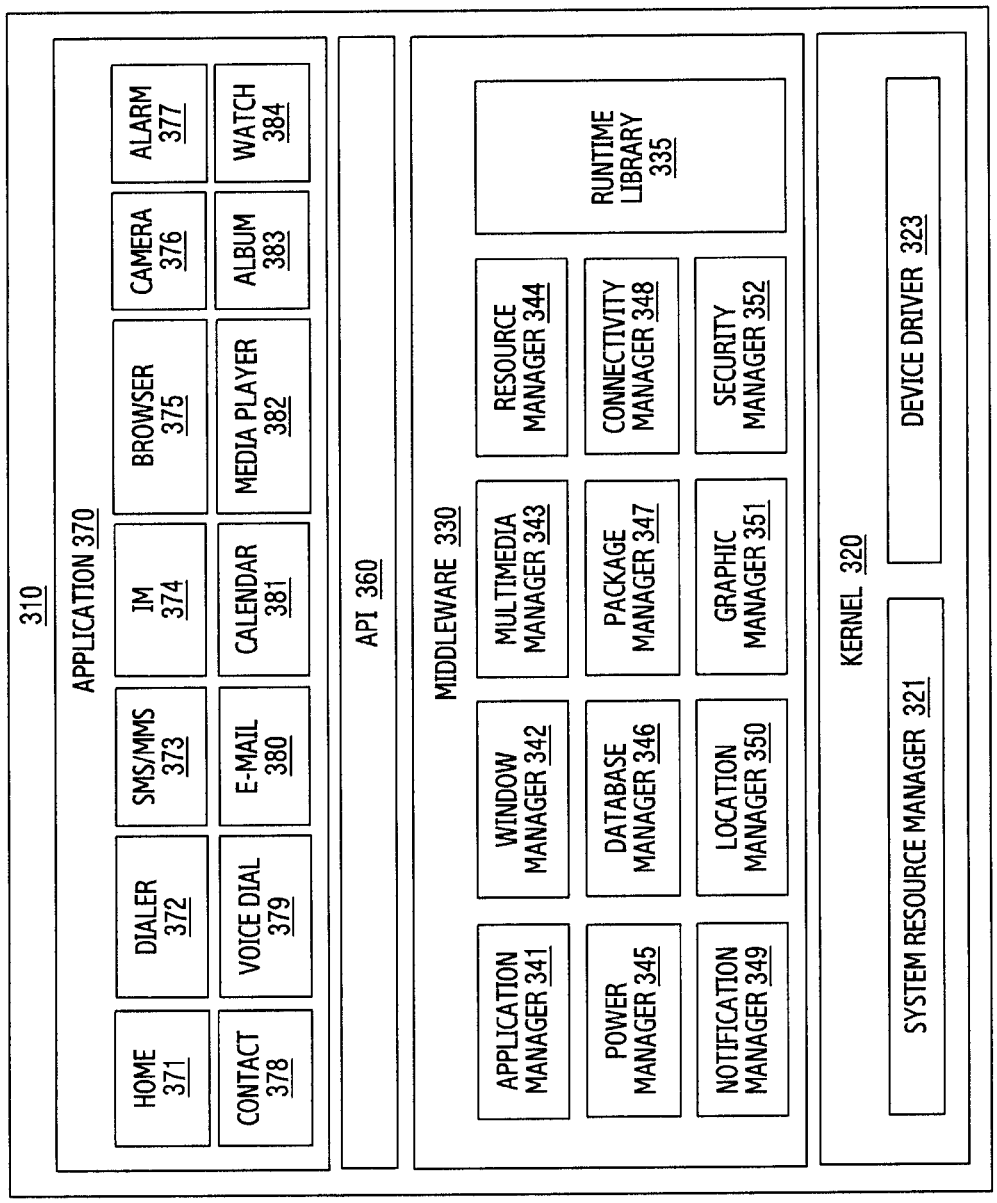
FIG. 3 is a block diagram of a program module according to various embodiments.

FIG. 3 is a block diagram of a program module according to various embodiments of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, Android™, iOS™, Windows™, Symbian™, Tizen™, Bada™, or the like. The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

For example, the middleware 330 may provide a function utilized in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format utilized for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like utilized for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as Wi-Fi or Bluetooth. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions utilized for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, contacts 378, a voice dial 379, an email 380, a calendar 381, a media player 382, an album 383, a clock 384, health care (e.g., measuring exercise quantity or blood sugar), or environment information (e.g., providing atmospheric pressure, humidity, or temperature information).

According to an embodiment of the present disclosure, the applications 370 may include an application (hereinafter, referred to as an "information exchange application" for convenience of description) that supports exchanging information between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (e.g., the electronic device 102 or 104), notification information generated from other applications of the electronic device 101 (e.g., an SMS/MMS application, an e-mail application, a health management application, or an environmental information application). Further, the notification relay application may receive notification information from, for example, an external electronic device and provide the received notification information to a user.

The device management application may manage (e.g., install, delete, or update), for example, at least one function of an external electronic device (e.g., the electronic device 102 or 104) communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance or the like) designated according to an external electronic device (e.g., attributes of the electronic device 102 or 104). According to an embodiment of the present disclosure, the applications 370 may include an application received from an external electronic device (e.g., the server 106, or the electronic device 102 or 104). According to an embodiment of the present disclosure, the applications 370 may include a preloaded application or a third party application that may be downloaded from a server. The names of the components of the program module 310 of the illustrated embodiment of the present disclosure may change according to the type of operating system.

According to various embodiments, at least a part of the programming module 310 may be implemented in software, firmware, hardware, or a combination of two or more thereof. At least some of the program module 310 may be implemented (e.g., executed) by, for example, the processor (e.g., the processor 210). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter. According to various embodiments, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable recoding media may be, for example, the memory 130.

Figure 4:
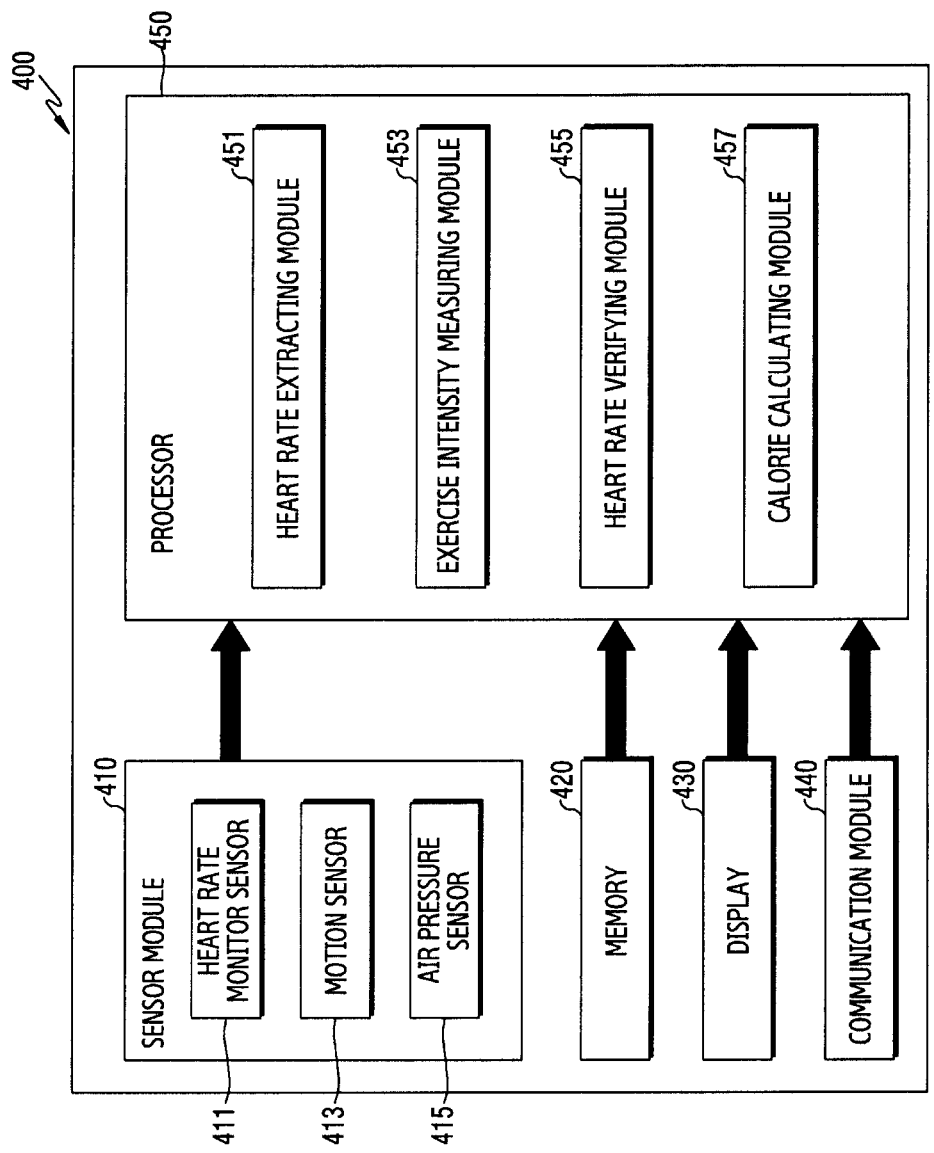
FIG. 4 is a block diagram of an electronic device according to various embodiments.

FIG. 4 is a block diagram of an electronic device according to various embodiments.

Referring to FIG. 4, the electronic device 400 (e.g., the electronic device 101) can include a sensor module 410, a memory 420, a display 430, a communication module 440, and a processor 450. The memory 420 can be included in the processor 450, or can be disposed outside the processor 450 and functionally coupled with the processor 450. The electronic device 400 can be worn on a user's body to detect a user's motion, like a wearable device. Alternatively, the electronic device 400 can receive sensor data from a wearable device including the sensor module 410 and predict heartbeat data (or heart rate).

The sensor module 410 can continuously or periodically sense information measured or detected according to the user's motion. The sensor module 410 can include at least one of a heart rate monitor sensor 411, a motion sensor 413, and an air pressure sensor 415. Such a sensor module 410 can be the sensor module 240 of FIG. 2. Accordingly, the sensor module 410 can further include other sensors not depicted in FIG. 4. The sensor module 410 can send the measured or detected sensor data (e.g., acceleration data, air pressure data) or heart rate data to the processor 450.

The heart rate monitor sensor 411 can measure user's heartbeat data. For example, the heart rate monitor sensor 411 can include at least one of an optical sensor, an Electrocardiogram (ECG) sensor and a Photoplethysmography (PPG) sensor. When the heart rate monitor sensor 411 is the optical sensor, the heart rate monitor sensor 411 can include a light emitter and a light receiver. The light emitter can include at least one of Infrared (IR), a red Light Emitting Diode (LED), a green LED, and a blue LED, and the light receiver can include a photodiode. When the electronic device 400 is attached to the user's body, the light emitter of the heart rate monitor sensor 411 can output the light, and the light receiver can detect the output light reflected by at least part of the user's body. For example, to determine user's blood flow variance, the light can go deeper than a user's kin (e.g., to a blood vessel) and then be reflected. The heart rate monitor sensor 411 can digitize light amounts detected by the light receiver, arrange them in sequence, and thus generate a signal. The heart rate monitor sensor 411 can send the generated signal to the processor 450. Notably, the generated signal can include various noises in addition to a frequency measured by the user's heartbeat.

Alternatively, the PPG sensor can utilize changes in the light absorption and reflection according to variance of a blood vessel thickness based on the heartbeat. When the heart rate monitor sensor 411 is the PPG sensor, the heart rate monitor sensor 411 can include a light emitter which emits IR, and a light receiver which detects the light emitted to and reflected from the user's body. The heart rate monitor sensor 411 can detect a PPG signal from the changes of the blood flow volume optically detected by the light receiver based on time.

The motion sensor 413 can include an acceleration sensor or a gyro sensor. For example, the acceleration sensor measures acceleration on x, y, and z axes, and can predict a force exerted on the electronic device using the measured acceleration. For example, when the acceleration sensor detects no motion, a value corresponding to gravitational acceleration is produced. When the acceleration sensor detects a motion, vibrations in a movement direction can be exhibited as variance of the force, that is, variance of the acceleration. An acceleration change pattern varies according to an exercise type of the user, and a unique pattern can emerge per exercise. The motion sensor 413 can send the measured acceleration data to the processor 450.

The air pressure sensor 415 can detect an altitude change of the electronic device 400. For example, the air pressure sensor 415 can measure whether the user is moving to a high altitude or to a low altitude. During an indoor exercise on a treadmill, an indoor cycle, an elliptical trainer, or a rowing machine, its motion is detected by the acceleration sensor but the altitude change is not detected by the air pressure sensor 415 (e.g., no variance in air pressure data). Unlike the indoor exercise, an outdoor exercise such as walking or running can change the altitude (e.g., change in the air pressure data). In this case, the acceleration sensor can detect the motion and the air pressure sensor 415 can detect the altitude change. The air pressure sensor 415 can send the measured air pressure data to the processor 450.

The processor 450 can process operations or data for control or communication of at least one component (e.g., the sensor module 410, the memory 420, the display 430, or the communication module 440) of the electronic device 400. For example, the processor 450 can predict (or estimate) a user motion state (e.g., exercise type) such as walking or running, using an acceleration pattern, and process it into pedometer information. Using the sensor data of the air pressure sensor 415 together with the motion sensor 413, the processor 450 can specify the exercise (e.g., the exercise type) of the user. The processor 450 can be the processor 120 of FIG. 1 or the processor 210 of FIG. 2. The processor 450 can include a heart rate extracting module 451, a heart rate verifying module 455, an exercise intensity measuring module 453, and a calorie calculating module 457.

The heart rate extracting module 451 can extract the frequency corresponding to the heart rate (or heartbeat data) from the signal received from the heart rate monitor sensor 411. The heart rate extracting module 451 can remove noise from the received signal using various processes. For example, the heart rate extracting module 451 can cancel the frequency according to the user motion and thus reduce interference between frequencies. Besides the user motion, various external factors can cause inaccurate heartbeat data measured. For example, when the heart rate monitor sensor 411 is not precisely attached to a user's body part and a space exists between the skin and the heart rate monitor sensor 411, other value than the value reflected from the skin can be input to the light receiver. In this case, accurate heartbeat data may not be acquired merely by removing the frequency of the user motion. To obtain the accurate heart rate (or heartbeat data), the processor 450 can use the heart rate verifying module 455.

The exercise intensity measuring module 453 can measure a user's exercise intensity using the sensor data received from the motion sensor 413 or the air pressure sensor 415. For example, when the electronic device 400 is a wearable device, a wearing position of the wearing device on the user can vary and accordingly motion sensor data measured by the motion sensor 413 or the air pressure sensor 415 can differ according to the device wearing position and a current user exercise type. That is, since the motion sensor data changes according to the device wearing position or the exercise type, an exercise intensity measurement model can differ. The exercise intensity measuring module 453 can measure the exercise intensity based on the motion sensor data and the exercise type. The measured exercise intensity can be used to predict and verify the heartbeat data in the heart rate verifying module 455.

The heart rate verifying module 455 can verify the heartbeat data extracted by the heart rate extracting module 451. The heart rate verifying module 455 can use the exercise intensity relating to the user motion as a leading indicator. For example, when the user performs a high-intensity exercise, the heartbeat data can rise according to a level. When the user performs a low-intensity exercise, the heartbeat data can decrease according to a level. The heart rate verifying module 455 can predict how next heartbeat data changes based on at least one of changes of heartbeat data previously measured in real time, and the exercise intensity. The heart rate verifying module 455 can compare the predicted heartbeat data with the measured heartbeat data and thus determine whether the current heartbeat data measured is accurate or not.

The heart rate verifying module 455 according to various embodiments can determine an exercise type using first motion sensor data acquired by the motion sensor 413 for a first duration, and determine a heartbeat prediction range based on at least one of the first motion sensor data, the exercise type, and first heartbeat data obtained from the heart rate monitor sensor 411 for the first duration. The heart rate verifying module 455 can determine whether second heartbeat data obtained from the heart rate monitor sensor 411 for a second duration is included in the heartbeat prediction range, and determine heartbeat data of the second duration based on the determination result. The heart rate verifying module 455 according to various embodiments can determine at least one of a maximum value, a minimum value, and an average value of the heartbeat prediction range, as third heartbeat data.

The calorie calculating module 457 can calculate calories based on the heartbeat data verified by the heart rate verifying module 455. The calorie calculating module 457 according to various embodiments can calculate the calories using the heartbeat data using the exercise type, or calculate the calories using the motion sensor data and the heartbeat data. Also, the calorie calculating module 457 can calculate the calories by further using at least one of location information, sensor data (e.g., acceleration data, air pressure data), and pedometer data in addition to the heartbeat data.

The processor 450 according to various embodiments can include a first processor and a second processor. The first processor can operate (e.g., activate, operation mode) when power is applied to the electronic device 400. While the power is applied to the electronic device 400, the first processor can wake up and receive the sensor data from the sensor module 410. The first processor can be awake regardless on/off of the display 430 of the electronic device 400. The first processor can drive with lower power than the second processor. The first processor can determine user exercise information based on the sensor data. The first processor can send the determined user exercise information to the second processor.

The second processor can selectively operate if desired. For example, when the display 430 is turned on, information is obtained, or information is scanned, the second processor can activate (e.g., operation mode). Also, when the display 430 is turned off, the second processor can deactivate (e.g., sleep mode). That is, the second processor can operate in the inactive state (e.g., sleep mode), and wake up and activate according to at least one of a periodic basis, a preset scanning period, and an application operation period (or application information request).

The second processor can obtain communication information through the communication module 440 and send the data obtained from the calorie calculating module 457. For example, the communication module 440 can send the data (e.g., heartbeat data, calories) obtained from the calorie calculating module 457 to another electronic device (e.g., a smart phone, a server, etc.) using at least one communication scheme (e.g., BT, WiFi, NFC, cellular, etc.). The communication module 440 can be the communication module 220 of FIG. 2. The display 430 can display various information relating to the heartbeat data. For example, the display 430 can display at least one of the heartbeat data, the motion sensor data, and the calories in detail or based on time according to a user input (e.g., touch input, button/key/wheel input). The display 430 can be the display 260 of FIG. 2.

According to various embodiments, the electronic device 400 can include a motion sensor 413, a heart rate monitor sensor 411, and a processor 450 functionally coupled with the motion sensor 413 and the heart rate monitor sensor 411. The processor 450 can be configured to obtain first motion sensor data for a first duration using the motion sensor 413, to obtain first heartbeat data for the first duration using the heart rate monitor sensor 411, to determine an exercise type based on the first motion sensor data, to determine a heartbeat prediction range based on at least one of the first motion sensor data, the exercise type, and the first heartbeat data, to obtain second heartbeat data for a second duration using the heart rate monitor sensor, to determine whether the second heartbeat data falls within the heartbeat prediction range, and to determine heartbeat data of the second duration based on the determination result.

The processor 450 can determine the second heartbeat data as the heartbeat data of the second duration when the second heartbeat data falls within the heartbeat prediction range, and determine third heartbeat data in the heartbeat prediction range as the heartbeat data of the second duration when the second heartbeat data does not fall within the heartbeat prediction range.

When the second heartbeat data does not fall within the heartbeat prediction range, the processor 450 can determine the third heartbeat data based on a maximum value and a minimum value of the heartbeat prediction range, and the second heartbeat data, and correct the second heartbeat data with the third heartbeat data.

The processor 450 can determine at least one of the maximum value, the minimum value, and an average value of the heartbeat prediction range, as the third heartbeat data.

When the second heartbeat data falls within the heartbeat prediction range, the processor 450 can calculate calories using the second motion sensor data or the second heartbeat data obtained in the second duration, and when the second heartbeat data does not fall within the heartbeat prediction range, the processor 450 can calculate calories using the second motion sensor data obtained in the second duration or the third heartbeat data within the heartbeat prediction range.

Based on the exercise type, the processor 450 can calculate the calories using the first heartbeat data, or calculate the calories using the first motion sensor data and the first heartbeat data.

The processor 450 can determine an exercise intensity or the exercise type based on the first motion sensor data, determines predicted heartbeat data based on at least one of the exercise intensity, the exercise type, and the first heartbeat data, and determine the heartbeat prediction range by considering a margin of error based on the predicted heartbeat data.

The first motion sensor data can include acceleration data, and the processor 450 can determine the exercise intensity or the exercise type according to acceleration variance based on the acceleration data or variance of air pressure data using an air pressure sensor 415.

With the variance of the air pressure data, the processor 450 can determine the predicted heartbeat data by adjusting a weight which reflects the acceleration variance on the exercise intensity.

Without the variance of the air pressure data, the processor 450 can determine the predicted heartbeat data to correspond to changes of the acceleration variance.

The processor 450 can set different margins of error according to the predicted heartbeat data.

The processor 450 can determine the heartbeat prediction range by further considering user body information.

The processor 450 can calculate first calories of the first duration using the first motion sensor data or the first heartbeat data, and display a user interface regarding at least one of the first motion sensor data, the first heartbeat data, and the first calorie, through a display of the electronic device.

The processor 450 can include a first processor and a second processor, the first processor can be activated, and the second processor can be selectively activated.

The electronic device 400 can be worn on a user body.

Figure 5:
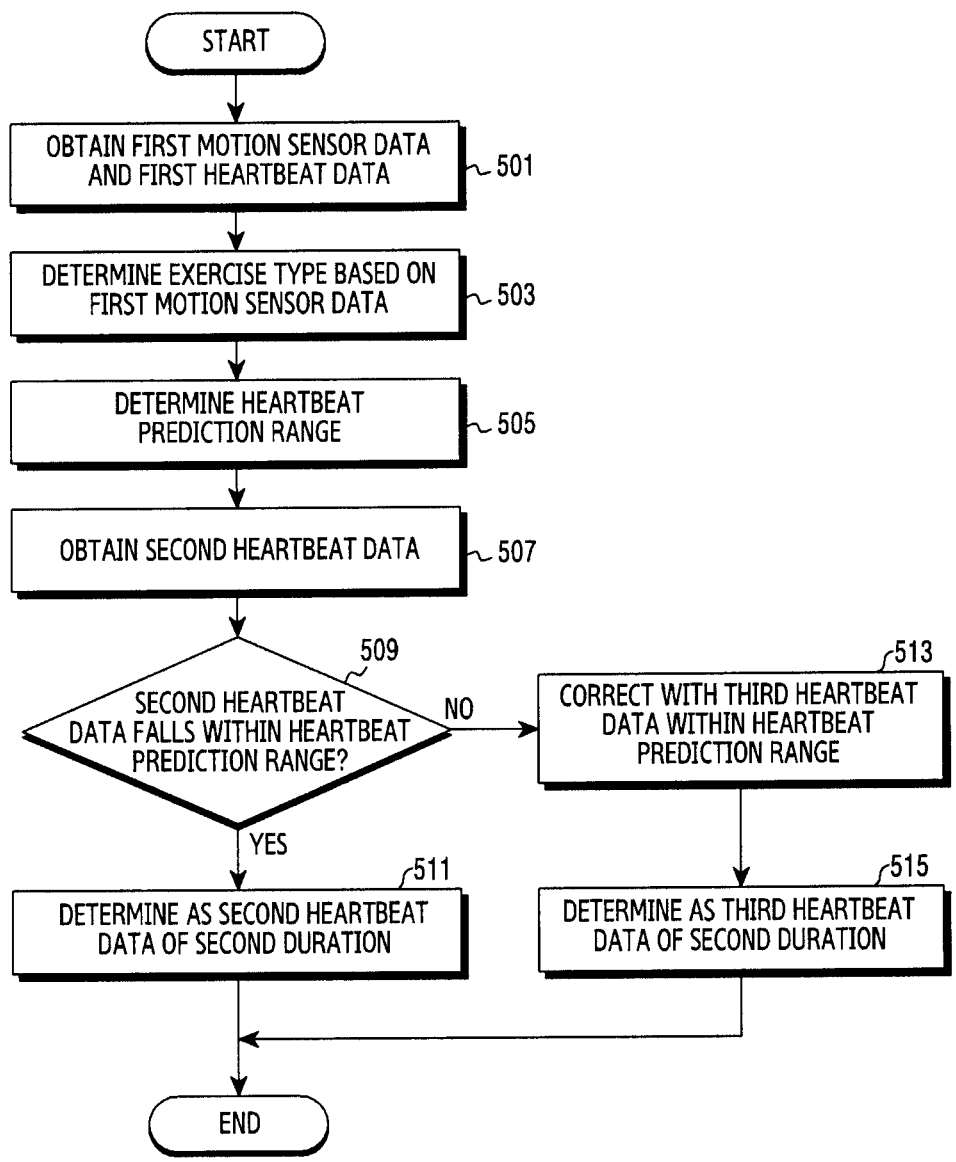
FIG. 5 is a flowchart of an operating method of an electronic device according to various embodiments.

FIG. 5 is a flowchart of an operating method of an electronic device according to various embodiments.

Referring to FIG. 5, in operation 501, the electronic device 400 (e.g., the processor 450) can obtain first motion sensor data and first heartbeat data. The first motion sensor data can be obtained (or received) from the motion sensor 413. The first heartbeat data can be obtained (or received) from the heart rate monitor sensor 411. The processor 450 can obtain or receive air pressure data from the air pressure sensor 415.

The processor 450 according to various embodiments can calculate the first motion sensor data using sensor data obtained from the motion sensor 413, and calculate the first heartbeat data using sensor data obtained from the heart rate monitor sensor 411. The processor 450 can remove noise from the obtained sensor data, and calculate the first motion sensor data and the first heartbeat data using the noise-free sensor data. For example, the processor 450 can cancel noise detected in the sensor data using a low pass filter, an average filter, and so on. Besides, the processor 450 can remove noise from the sensor data using various noise reduction filters.

According to various embodiments, the processor 450 can determine, using data received from the sensor module 410, whether the user has initiated execution of an exercise (or some physical activity). For example, when the sensor data obtained from the sensor module 410 exceeds a predetermined threshold (e.g., a motion level, an acceleration change level, etc.), the processor 450 can determine that the user has initiated exercise. For example, when a motion detected exceeds the preset threshold of the sensor data or a repeated motion pattern is detected, the processor 450 can determine that the user has initiated exercise. Alternatively, when the user directly selects an "exercise start button" through an input/output interface (e.g., the input/output interface 150), the processor 450 can determine that the user has initiated exercise. The first motion sensor data and the first heartbeat data can be obtained for a first duration (e.g., time point). For example, the first duration can be a preset time (e.g., 5 minutes, 10 minutes, etc.) after the user exercise start is determined.

In operation 503, the electronic device 400 (e.g., the processor 450) can determine a particular type of exercise routine or action being performed (e.g., an exercise type) based on the first motion sensor data. Mostly, the exercise type can include an isometric exercise, an isotonic exercise, an isokinetic exercise, an anaerobic exercise, and an aerobic exercise. Among the exercise types, an exercise relating to the heartbeat or the calorie consumption corresponds to the aerobic exercise and accordingly the aerobic exercise now is described by way of example. Notably, the present disclosure is not limited to those exercise types. The aerobic exercise can indicate, for example, walking, running, cycling, climbing, swimming, running on a treadmill, rowing, and elliptical training. That is, the aerobic exercise can indicate a regular or repeated exercise. To determine the exercise type, the motion sensor data can be utilized. The processor 450 (e.g., the exercise intensity measuring module 453) can determine an exercise intensity using the motion sensor data.

For example, for considerable acceleration variance, the processor 450 can determine a moderate exercise intensity and the running or the rowing as the exercise type. For small acceleration change, the processor 450 can determine a low exercise intensity and the walking or the elliptical training as the exercise type.

According to various embodiments, the processor 450 can determine the exercise intensity by considering variance of the air pressure data obtained from the air pressure sensor 415 together with the motion sensor data. For example, when the altitude increases (e.g., uphill) with the same exercise intensity, the acceleration variance can decrease. When the altitude decreases (e.g., downhill) with the same exercise intensity, the acceleration variance can increase. Hence, the processor 450 can calculate the exercise intensity by adjusting the acceleration variance based on the variance of the air pressure data. For acceleration variance and air pressure variance greater than respective variance preset thresholds, the processor 450 can determine the moderate exercise intensity and the exercise type as climbing (e.g., downhill walking or running). For acceleration variance and air pressure variance smaller than respective variance preset thresholds, the processor 450 can determine the high exercise intensity and the exercise type as climbing (e.g., uphill walking or running).

According to various embodiments, the processor 450 (e.g., the calorie calculating module 457) can calculate calories using the first heartbeat data. Alternatively, the processor 450 can calculate the calories using the first motion sensor data and the first heartbeat data. Since the first motion sensor data and the first heartbeat data are detected according to a user motion, the user can consume calories in a certain amount according to the movement. The processor 450 can calculate the calories (e.g., first calories) consumed by the user motion for the first duration. The processor 450 can calculate the calories using the first heartbeat data according to the exercise type, or calculate the calories using both of the first motion sensor data and the first heartbeat data. The processor 450 can provide a user interface relating to at least one of the first motion sensor data, the air pressure data, the first heartbeat data, and the first calories.

In operation 505, the electronic device 400 (e.g., the processor 450) can determine a heartbeat prediction range, or a predicted range in which the user's heartbeat is exepcted to fall while executing the exercise. The processor 450 (e.g., the heart rate verifying module 455) can calculate predicted heartbeat data using at least one of the first motion sensor data, the exercise type, and the first heartbeat data. The processor 450 can determine the heartbeat prediction range by considering a margin of error based on the predicted heartbeat data. For example, when the predicted heartbeat data is 100, the processor 450 can determine the heartbeat prediction range as 90~110 based on the margin of error of ±1.

According to various embodiments, the processor 450 can measure the exercise intensity based on the first motion sensor data. The exercise intensity is the leading indicator of the heartbeat data. For a "high" exercise intensity, the heartbeat data can rise to a level corresponding to the exercise intensity. For a "low" exercise intensity, the heartbeat data can fall to a level corresponding to the exercise intensity. Using the exercise intensity, the processor 450 can estimate how the heartbeat data will change. Also, based on the first motion sensor data, the processor 450 can determine the exercise type. For the high exercise intensity, the heartbeat data to be measured can change more than the current heartbeat data or maintain a high level. Alternatively, for the low exercise intensity, the heartbeat data to be measured can change less than the current heartbeat data. Depending on how long the exercise continues, the heartbeat data can change considerably or maintain a low level according to the exercise intensity. Since the heartbeat data is the heart rate of the user and the heart rate changes according to the exercise with a certain variance range, a next heart rate can be predicted based on the current heart rate. The variance of the heartbeat data can be greater or smaller than a certain threshold, according to whether the current heartbeat data reaches a certain limit.

According to various embodiments, the processor 450 can determine the heartbeat prediction range by further considering user's body information. For example, the user's body information can include various information about the user, such as height, weight, age, gender, resting heart rate, blood pressure, body fat, and blood type. For example, the blood pressure can differ according to the age or the gender, or according to a user's current condition. The blood pressure can affect the heartbeat data. A maximum heart rate can be determined based on the age, and the age can affect the heartbeat data and the calories. Hence, the processor 450 can determine an accurate heartbeat prediction range by further using the user body information together with the measured motion sensor data and heartbeat data. For doing so, the processor 450 can request the user to pre-input his/her body information. Alternatively, the processor 450 can analyze the body information based on user's use record, without having to pre-registering the body information of the user. For example, the processor 450 can extract body information registered by the user in a health application installed on the electronic device 400.

In operation 507, the electronic device 400 (e.g., the processor 450) can obtain second heartbeat data. The second heartbeat data can be sensor data obtained from the heart rate monitor sensor 411 for a second duration (e.g., 09:06~09:10) after the first duration (e.g., 09:00~09:05). The processor 450 can calculate the second heartbeat data using a second set of sensor data obtained from the heart rate monitor sensor 411. The processor 450 can obtain a second set of motion sensor data from the motion sensor 413 and the air pressure sensor 415 for the second duration (or time point). The first duration or the second duration can include a certain duration or a specific time point. The second duration can be shorter than the first duration. That is, the first duration can include a certain duration (e.g., 5 minutes), and the second duration can include a time point (e.g., 09:06).

In operation 509, the electronic device 400 (the processor 450) can determine whether the second heartbeat data indicates a heartbeat rate falling within the heartbeat prediction range. When the heart rate monitor sensor 411 is attached to a user's chest, the heartbeat data can be measured accurately. Otherwise, the measured heartbeat data can be inaccurate. This is because, when the heart rate monitor sensor 411 measures the heartbeat data, various external factors (e.g., user's movement, sensor attached or detached, etc.) can cause the inaccurate heartbeat data. The heartbeat prediction range can predict next heartbeat data using the exercise intensity, the exercise type, and the current heartbeat data. Hence, the predicted heartbeat data can be more accurate than the measured heartbeat data.

When the second heartbeat data falls within the heartbeat prediction range, the processor 450 (e.g., the heart rate verifying module 455) can perform operation 511. When the second heartbeat data does not fall within the heartbeat prediction range, the processor 450 can perform operation 513.

When the second heartbeat data falls within the heartbeat prediction range, the electronic device 400 (e.g., the processor 450) can determine the obtained second heartbeat data as the heartbeat data of the second duration in operation 511. The processor 450 can calculate calories (e.g., second calories) using the second motion sensor data or the second heartbeat data. Based on the exercise type, the processor 450 can calculate the calories using the second heartbeat data, or calculate the calories using second motion sensor data or the second heartbeat data. The processor 450 can calculate calories (e.g., the second calories) consumed by the user motion during the second duration. The processor 450 can provide a user interface relating to at least one of the second heartbeat data, the second heartbeat data, and the second calories.

When the second heartbeat data does not fall within the heartbeat prediction range, the electronic device 400 (e.g., the processor 450) can correct it with third heartbeat data within the heartbeat prediction range in operation 513. As mentioned earlier, the predicted heartbeat data (e.g., the heartbeat data within the heartbeat prediction range) can be more accurate than the measured heartbeat data (e.g., the second heartbeat data). When the second heartbeat data obtained in the second duration does not fall within the heartbeat prediction range, the processor 450 can correct the second heartbeat data with the third heartbeat data of the heartbeat prediction range. The third heartbeat data is included in the heartbeat prediction range, and the processor 450 can determine the third heartbeat data based on a maximum value and a minimum value of the heartbeat prediction range and the second heartbeat data. For example, the processor 450 can determine at least one of the maximum value, the minimum value, and an average value of the heartbeat prediction range, as the third heartbeat data.

In operation 515, the electronic device 400 (e.g., the processor 450) can determine the corrected third heartbeat data as the heartbeat data of the second duration. The processor 450 can calculate the calories using the second motion sensor data or the third heartbeat data. Based on the exercise type, the processor 450 can calculate the calories using the third heartbeat data, or calculate the calories using second motion sensor data and the third heartbeat data. The processor 450 can calculate the calories (e.g., the second calories) consumed by the user motion during the second duration. The processor 450 can provide a user interface relating to at least one of the second heartbeat data, the third heartbeat data, and the second calories. When the measured heartbeat data is not accurate, the processor 450 can calculate the calories using the corrected heartbeat data and thus provide more accurate calories based on the user movement.

Figure 6A:
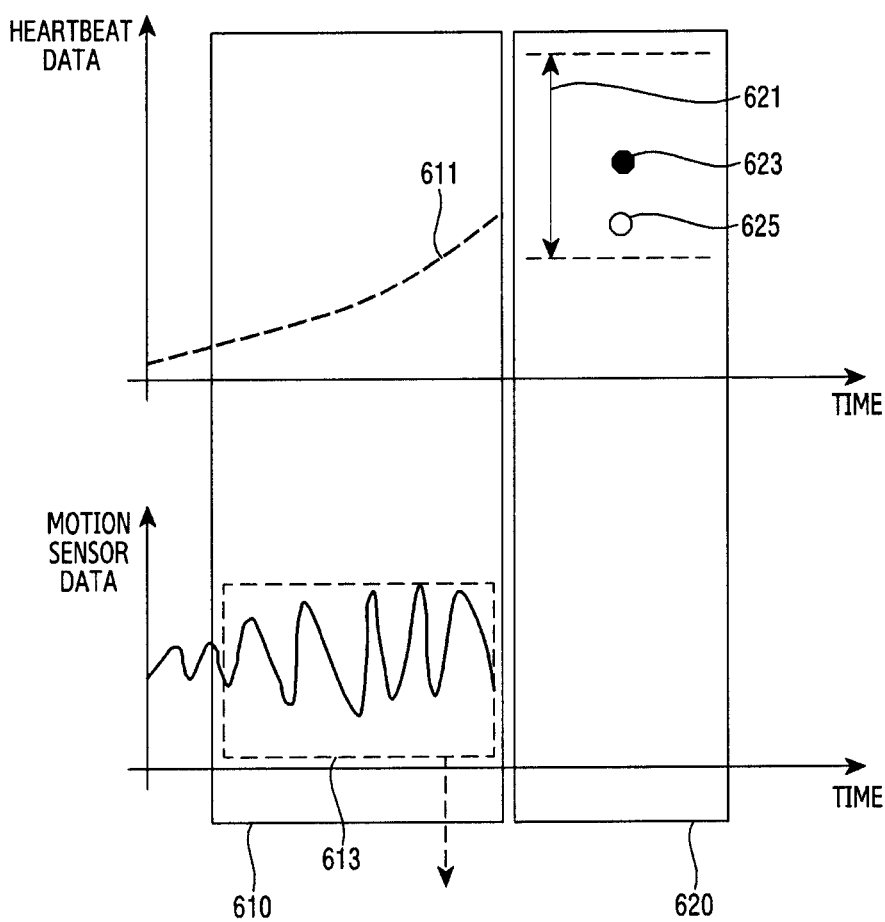
FIG. 6A and FIG. 6B are diagrams of heartbeat data predicted in an electronic device according to various embodiments.
Figure 6B:
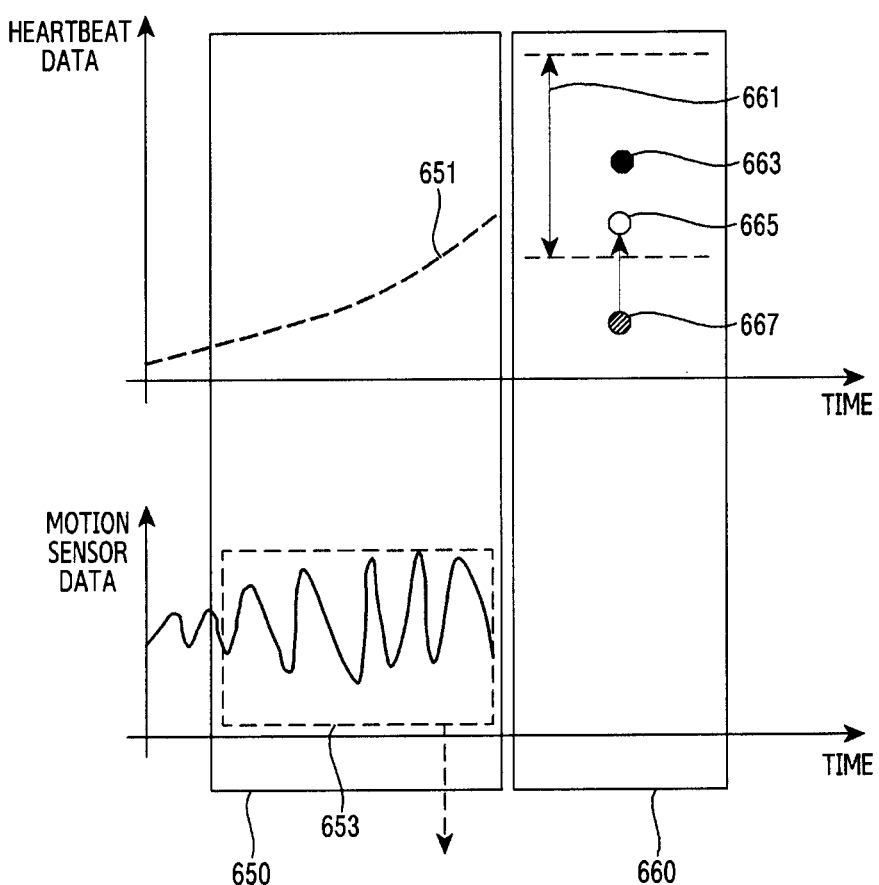

FIGS. 6A and 6B are diagrams of heartbeat data predicted in an electronic device according to various embodiments.

FIG. 6A depicts an example where a heartbeat prediction range covers second heartbeat data.

Referring to FIG. 6A, the electronic device 400 (e.g., the processor 450) can obtain first heartbeat data 611 and first motion sensor data 613 for a first duration 610. Herein, the motion sensor data 613 can be acceleration data obtained from an acceleration sensor. The first duration 610 can be a certain duration after the user begins an exercise. The processor 450 can predict second heartbeat data of a second duration 620 based on the first heartbeat data 611 and the first motion sensor data 613 of the first duration 610. For example, the processor 450 can measure a user exercise intensity using the first motion sensor data 613. The processor 450 can determine an exercise type based on the first motion sensor data 613, and determine a heartbeat prediction range 621 of the second duration 620 using at least one of the first motion sensor data 613, the determined exercise type, and the first heartbeat data 611. For example, the heartbeat prediction range 621 can be set to a value of a certain range by considering a margin of error in predicted heartbeat data 623. The processor 450 can obtain second heartbeat data 625 from the heart rate monitor sensor 411 for the second duration 620. When the second heartbeat data 625 falls within the heartbeat prediction range 621, the processor 450 can use the second heartbeat data 625 to calculate caloric consumption.

FIG. 6B depicts an example where a heartbeat prediction range does not encapsulate the detected second heartbeat data.

Referring to FIG. 6B, as in the preceding, the electronic device 400 (e.g., the processor 450) can obtain first heartbeat data 651 and first motion sensor data 653 for a first duration 650. Herein, the motion sensor data 653 can be acceleration data obtained from an acceleration sensor. The processor 450 can predict second heartbeat data of a second duration 660 based on the first heartbeat data 651 and the first motion sensor data 653 of the first duration 650. For example, the processor 450 can determine an exercise type based on the first motion sensor data 653, and determine a heartbeat prediction range 661 of the second duration 660 using at least one of the first motion sensor data 653, the determined exercise type, and the first heartbeat data 651. For example, the heartbeat prediction range 661 can be set to a value of a certain range by considering a margin of error in predicted heartbeat data 663. The processor 450 can obtain second heartbeat data 667 from the heart rate monitor sensor 411 for the second duration 660. When the second heartbeat data 667 does not fall within the heartbeat prediction range 661, the processor 450 can correct the second heartbeat data 667 using third heartbeat data 665. The third heartbeat data 665 can be included in the heartbeat prediction range 661.

According to various embodiments, the processor 450 can determine the third heartbeat data 665 as heartbeat data to use for the measurement based on a maximum value and a minimum value of the heartbeat prediction range 661 and the second heartbeat data 667. For example, when the second heartbeat data 667 is close to the minimum value (e.g., when the second heartbeat data 667 is smaller than the minimum value), the processor 450 can determine the third heartbeat data 665 to a value between the minimum value and the predicted heartbeat data 663. Alternatively, when the second heartbeat data 667 is close to the maximum value (e.g., when the second heartbeat data 667 is greater than the maximum value), the processor 450 can determine the third heartbeat data 665 to a value between the maximum value and the predicted heartbeat data 663. The processor 450 can calculate calories using the third heartbeat data 665 in the second duration 660.

FIGS. 7A through 7D are diagrams of heartbeat data measured variously according to an exercise type according to various embodiments.

Figure 7A:
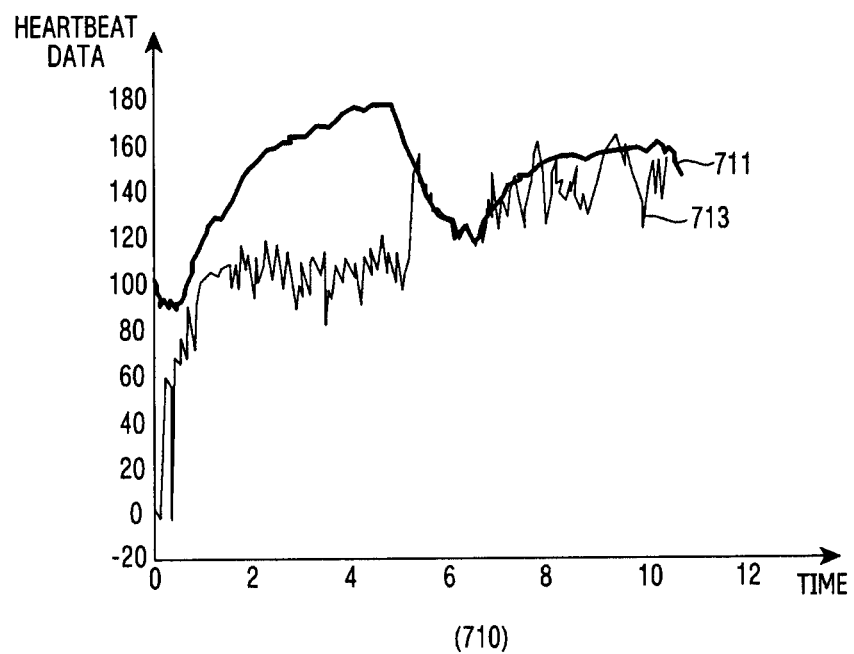
FIG. 7A, FIG. 7B, FIG. 7C and FIG. 7D are diagrams of heartbeat data measured variously according to an exercise type according to various embodiments.
Figure 7A:
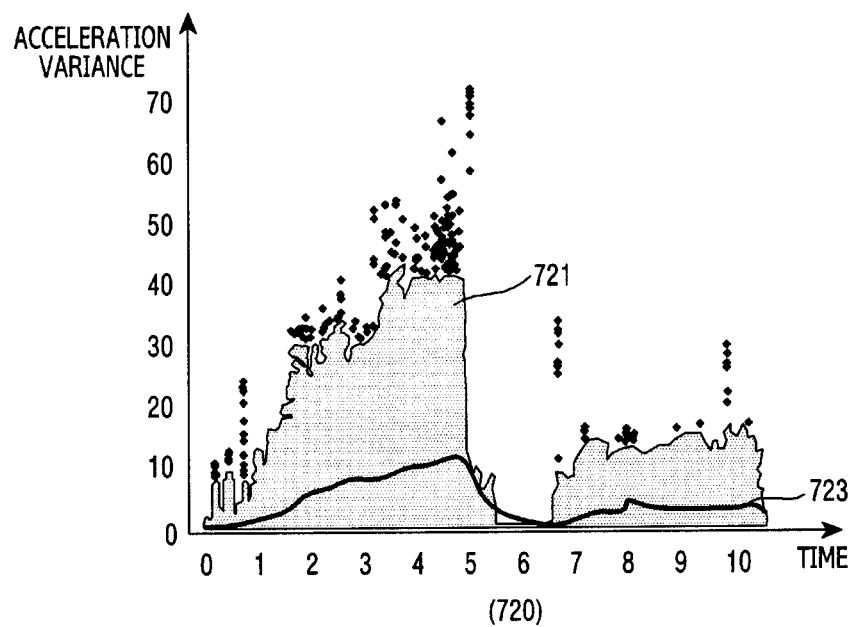

FIG. 7A depicts a heartbeat graph 710 and an acceleration variance graph 720 of a user who performs an elliptical exercise.

Referring to FIG. 7A, the heartbeat graph 710 shows the heartbeat data (or heart rate) of the user who performs the elliptical exercise rapidly for seven minutes, takes a rest for three minutes, and does the exercise slowly for six minutes. First heartbeat data 711 can be measured normally, and second heartbeat data 713 can be measured abnormally. The acceleration variance graph 720 shows variance 721 of values produced by normalizing sensor data (e.g., acceleration sensor) obtained from the motion sensor 413 during the user's elliptical exercise. Variance changes 723 can apply a low pass filter to the variance 721.

Comparing the heartbeat graph 710 and the acceleration variance graph 720, the first heartbeat data which is the normal heartbeats is quite similar to the variance changes 723. For example, when an acceleration variance level reaches '10', the value of the first heartbeat data 711 arrives at about 180. When the variance level reaches '3', the first heartbeat data 711 arrives at about 160 and then maintains a certain level. However, the second heartbeat data 713 does not correspond to the acceleration variance changes 723 at all, but increases when the variance level gets low.

The processor 450 can express relationship between the acceleration variance and the heartbeat data with respect to the elliptical exercise as Equation 1. The processor 450 can predict the user's heartbeat data in the elliptical exercise based on Equation 1.

$$C_{Elliptical} \propto (AccVar_i - AccVar_{i-1}) \qquad (1)$$

$$C_{Elliptical} \propto \frac{1}{AccVar_i}$$

Figure 7B:
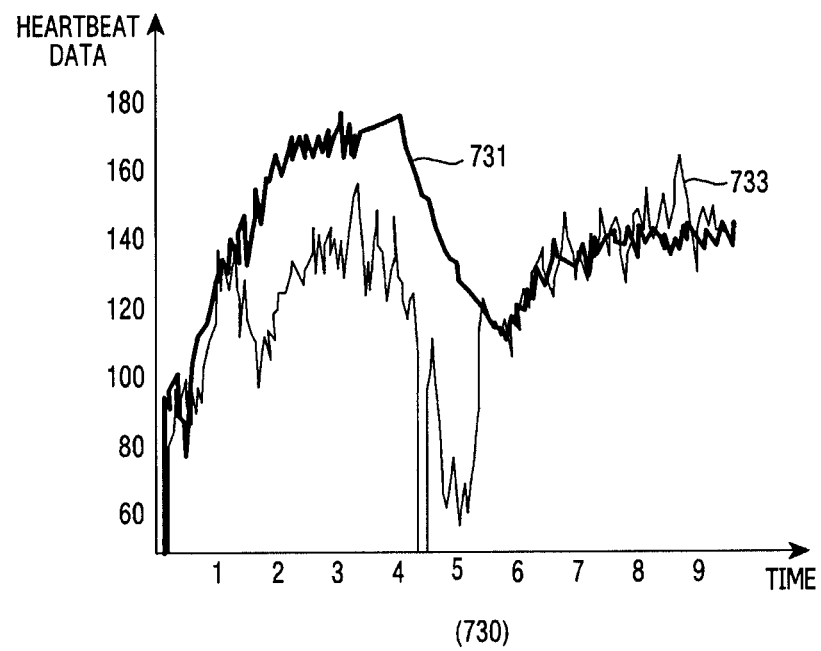
Figure 7B:
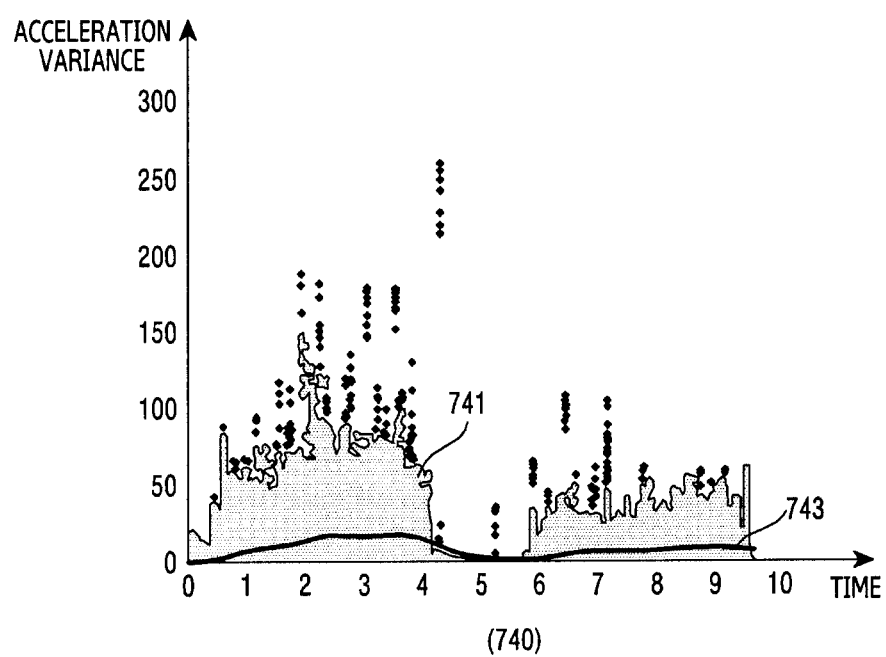

$C_{Elliptical}$: elliptical exercise coefficient
$AccVar_i$: average value of acceleration norm variance FIG. 7B depicts a heartbeat graph 730 and an acceleration variance graph 740 of a user who exercises on a rowing machine.

Referring to FIG. 7B, the heartbeat graph 730 shows heartbeat data (or heart rate) of the user who exercises on the rowing machine rapidly for six minutes, takes a rest for three minutes, and does the exercise slowly for six minutes. First heartbeat data 731 can be measured normally, and second heartbeat data 733 can be measured abnormally. In the acceleration variance graph 740, the acceleration variance 741 is greater than a preset threshold indicating the "hard" exercise, smaller than the preset threshold for the "light" exercise, and corresponds to the increase of the heartbeat data when the exercise intensity rises. Comparing the heartbeat graph 730 and the acceleration variance graph 740, when the light exercise continues, acceleration variance changes 743 and first heartbeat data 731 maintain a certain level. However, the second heartbeat data 733 abnormally measured changes regardless of the acceleration variance changes 743, and there is no relationship between the exercise intensity and the heartbeat data. Thus, when the changes of the heartbeat data do not follow the acceleration variance changes 743, the processor 450 can determine inaccurate measurement of the second heartbeat data 733.

The processor 450 can express the relationship between the acceleration variance and the heartbeat data in relation to the rowing machine as Equation 2. The processor 450 can predict the user's heartbeat data in the rowing machine exercise based on Equation 2.

$$C_{Rowing} \propto (AccVar_i - AccVar_{i-1}) \quad (2)$$
$$C_{Rowing} \propto \frac{1}{AccVar_i}$$

Figure 7C:
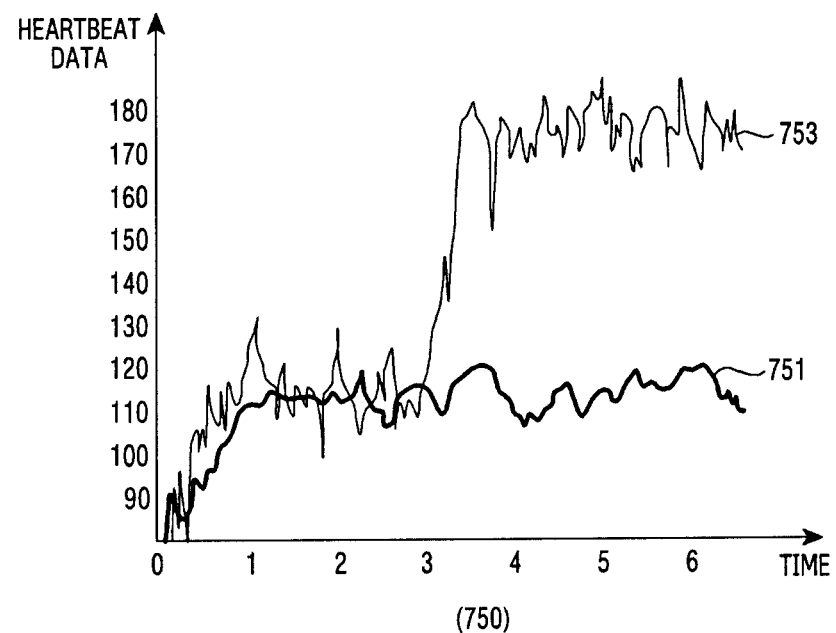
Figure 7C:
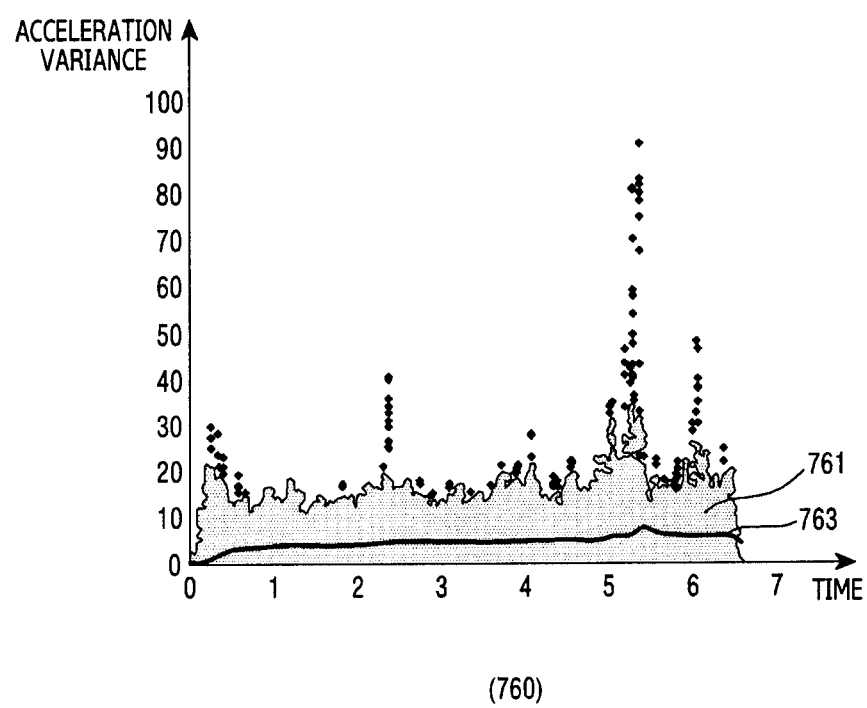

$C_{Rowing}$: rowing exercise coefficient
$AccVar_i$: average value of acceleration norm variance FIG. 7C depicts a heartbeat graph 750 and an acceleration variance graph 760 of a user who is walking.

Referring to FIG. 7C, the heartbeat graph 750 shows heartbeat data (or heart rate) when the user walks at a certain pace for ten minutes. First heartbeat data 751 can be measured normally, and the second heartbeat data 753 can be measured abnormally. The acceleration variance graph 760 shows acceleration variance 761 of values produced by normalizing sensor data (e.g., acceleration sensor) obtained from the motion sensor 413 during the user's walking. Variance changes 763 indicate the changes of the acceleration variance 761. When walking or running keeps a certain pace, the acceleration variance also maintains certain changes. Also, when a certain exercise intensity is maintained, the user's heartbeat data rises until it reaches a certain level and then maintains the level. This pattern can be also true for both of the walking and the running. Hence, when the heartbeat data abnormally increases or continuously increases while the acceleration variance 761 maintains the certain level, the processor 450 can determine the abnormal heartbeat data measured like the second heartbeat data 753. When the heartbeat data maintains a certain level, the processor 450 can predict that the heartbeat acceleration variance changes 763 continue similarly to the acceleration variance 761 while the acceleration variance 761 does not change.

Thus, the processor 450 can express the relationship between the acceleration variance and the heartbeat data in relation to the walking as Equation 3. The processor 450 can predict the user's heartbeat data during the walking based on Equation 3.

$$C_{WalkRun} \propto (AccVar_i - AccVar_{i-1}) \quad (3)$$
$$C_{WalkRun} \propto \frac{1}{AccVar_i}$$

Figure 7D:
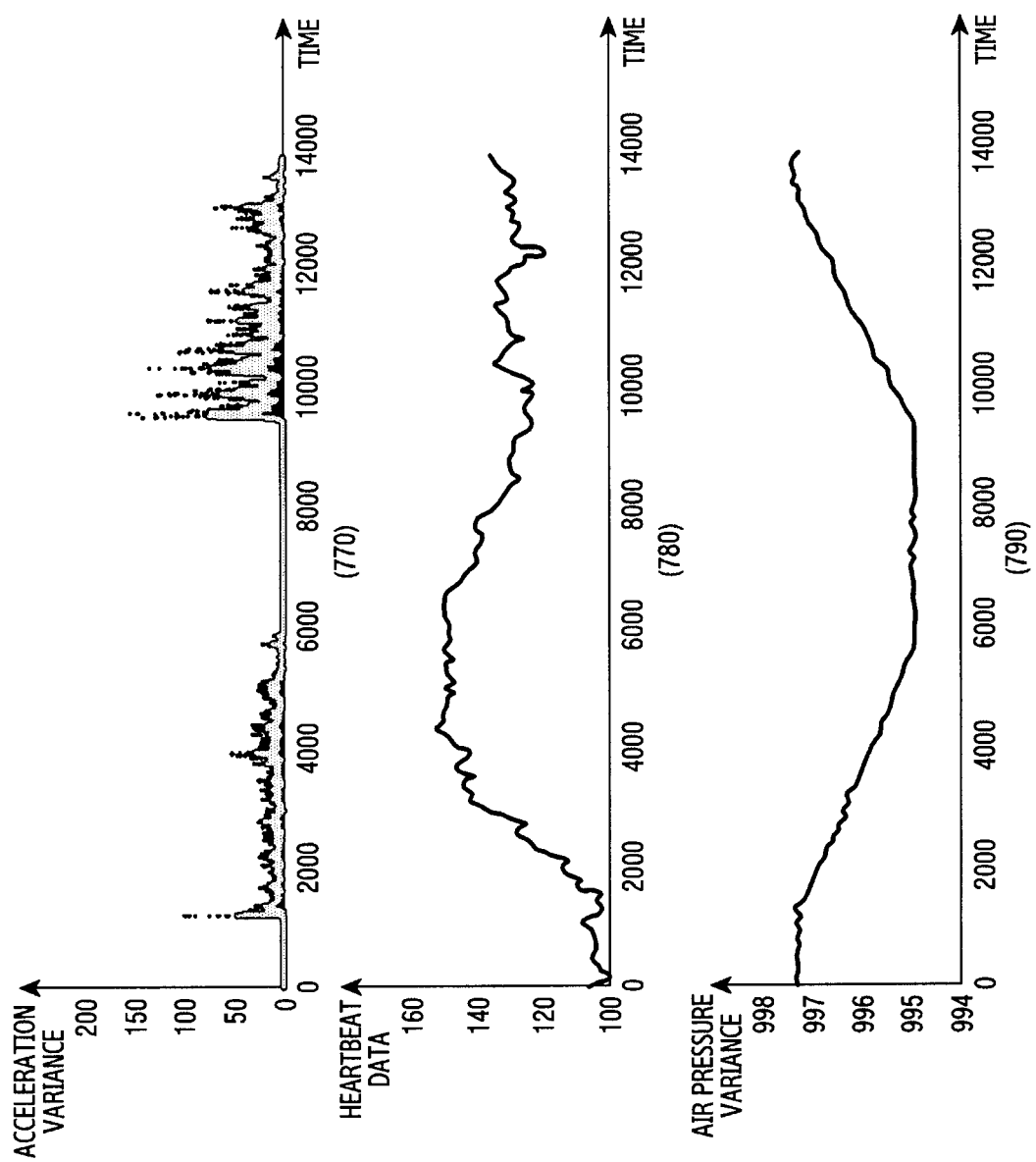

$C_{WalkRun}$: exercise coefficient of flat-surface walking/running
$AccVar_i$: average value of acceleration norm variance FIG. 7D depicts a heartbeat graph 780, an acceleration variance graph 770, and an air pressure graph 790 of a user who is walking on a slope.

Referring to FIG. 7D, the heartbeat graph 780 shows heartbeat data when the user walks up stairs to a fifth floor at a certain pace, takes a rest for one minute, and then walks down to the ground floor. The heartbeat data is reliable values obtained from the heart rate monitor sensor 411 over the same period. The acceleration variance graph 770 shows acceleration variance and acceleration variance changes of values produced by normalizing sensor data (e.g., acceleration sensor) obtained from the motion sensor 413 while the user walks up and down the stairs. The air pressure graph 790 shows sensor data obtained from the air pressure sensor 415 while the user walks up and down the stairs. Typically, the air pressure data can decrease by 0.36 hp or so when the user walks up one floor (3 m) and decrease when the user walks down the stairs.

Unlike other general exercises, the acceleration variance in the walking/running on the slope seems to be contrast to the heartbeat data variance. This is because the downhill climb has smaller acceleration variance than the uphill climb. Since the heartbeat data rises when the user climbs up (e.g., uphill), the processor 450 can determine based on the air pressure data whether the user is walking up or down. According to the uphill or downhill slope, the processor 450 can define a range of the acceleration variance.

Based on the heartbeat graph 780, the acceleration variance graph 770, and the air pressure graph 790, when the user walks up the stairs where the heartbeat data rises, the air pressure data value declines, the acceleration variance is constant, and the heartbeat data value increases. Next, when the user temporarily stops walking in order to climb down the stairs, the heartbeat data falls and the air pressure value is constant. When the user walks down the stairs, the air pressure data value increases and currently the acceleration variance level relatively rises. Notably, the heartbeat data value rises constantly, rather than sharply increasing in proportion to the increase of the acceleration variance.

Thus, the processor 450 can express the relationship between the acceleration variance, the air pressure variance, and the heartbeat data in relation to the slope walking as Equation 4. The processor 450 can predict the user's heartbeat data during the slope walking based on Equation 4.

$$C_{hiking} \propto (AccVar_i - AccVar_{i-1}) \quad (4)$$
$$C_{hiking} \propto (Pressure_{i-1} - Pressure_i)$$
$$C_{hiking} \propto \frac{1}{AccVar_i}$$

Figure 8:
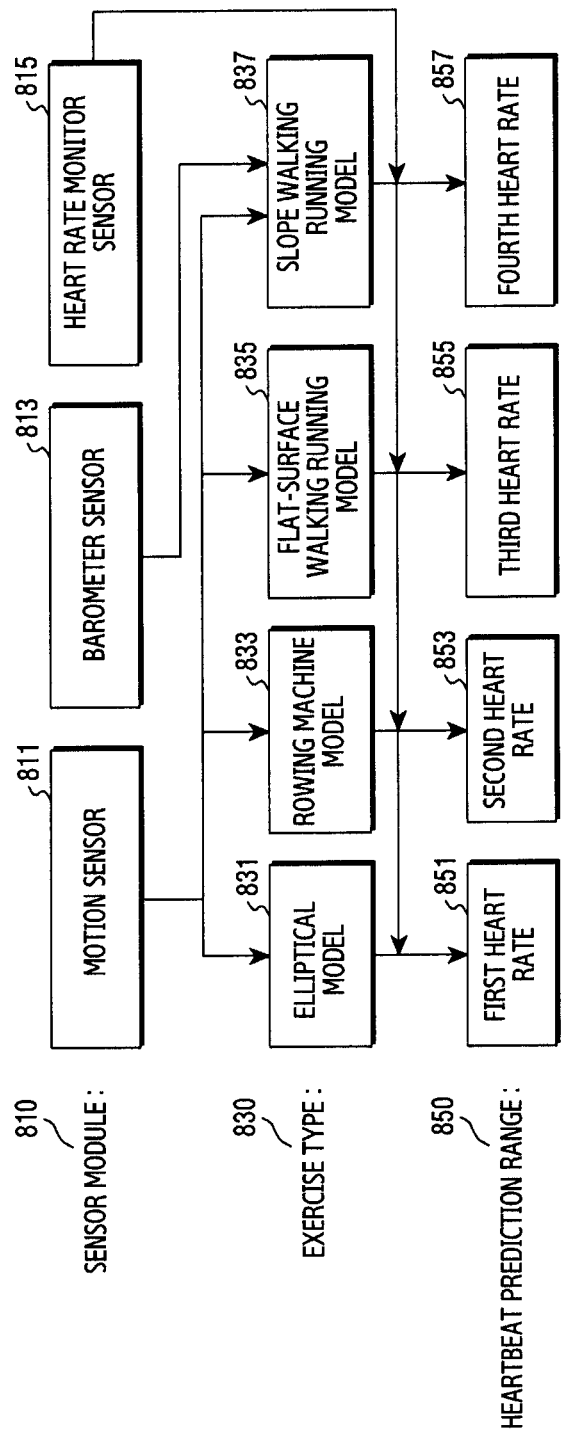
FIG. 8 is a diagram of a heartbeat prediction range determined based on an exercise type according to various embodiments.

$C_{Hiking}$: exercise coefficient of slope walking/running
$AccVar_i$: average value of acceleration norm variance
$Pressure_i$: air pressure measurement value FIG. 8 is a diagram of a heartbeat prediction range determined based on an exercise type according to various embodiments.

Referring to FIG. 8, the electronic device 400 (e.g., the processor 450) can determine an exercise type 830 using sensor data measured by a sensor module 810. For example, the processor 450 can determine at least one of elliptical exercise, rowing machine, flat-surface walking or running, and slope walking or running, as the exercise type 830 using an acceleration sensor 811 and an air pressure sensor 813. The processor 450 can calculate an exercise intensity using a different exercise model based on the exercise type 830. The exercise intensity is a leading indicator of heartbeat data. For a high exercise intensity, the heartbeat data can rise to a level corresponding to the exercise intensity. For a low exercise intensity, the heartbeat data can fall to a level corresponding to the exercise intensity. Using the exercise intensity, the processor 450 can estimate a next level of the heartbeat data. The exercise intensity can be measured using a normalizing value and variance of acceleration data. The heartbeat data also moves in proportion to the acceleration data, and its coefficient value or level can vary according to the user or the exercise type.

The exercise intensity differs according to the exercise type because a body part wearing the electronic device 400 differs and a motion varies according to the exercise. Referring back to FIGS. 7A, 7B, and 7C, when the acceleration variance increases, the heartbeat data increases. When the acceleration variance decreases, the heartbeat data reduces. When the acceleration variance maintains, the heartbeat data can reach a certain level and then maintains. Referring back to FIG. 7D, the acceleration is in inverse proportion to the exercise intensity, but the exercise intensity can be affected by the variance of the air pressure data. Using such features, the processor 450 can better determine whether currently measured heartbeat data is normal and predict next heartbeat data based on at least one of reliable previous heartbeat data, the acceleration variance, and the air pressure variance.

For example, when the exercise type is the elliptical training, the processor 450 can calculate the exercise intensity using an elliptical model 831. When the exercise type is the rowing machine, the processor 450 can calculate the exercise intensity using a rowing machine model 833. When the exercise type is the flat-surface walking or running, the processor 450 can calculate the exercise intensity using a flat-surface walking or running machine model 835. When the exercise type is the slope walking or running, the processor 450 can calculate the exercise intensity using a slope walking or running model 837. For the slope waking or running model 837, the processor 450 can calculate the exercise intensity using air pressure data obtained from the air pressure sensor 813. The processor 450 can determine a heartbeat prediction range 850 based on the exercise intensity, the exercise type 830, and the current heartbeat data. That is, for the high exercise intensity, next heartbeat data to be measured can vary more than the current heartbeat data or maintain. Alternatively, for the low exercise intensity, the next heartbeat data to be measured can vary less than the current heartbeat data or maintain. The variation of the heartbeat data based on the exercise intensity can increase or decrease according to how long the exercise is preformed or how drastically the exercise intensity changes.

Thus, the processor 450 can determine different heartbeat prediction ranges according to the exercise intensity, the exercise type, and the current heartbeat data. For example, the processor 450 can determine a first heart rate prediction range 851 of the elliptical training using the elliptical model 831 and the current heartbeat data obtained by a heart rate monitor sensor 815. The processor 450 can determine a second heart rate prediction range 853 of the rowing machine using the rowing machine model 833 and the current heartbeat data obtained by the heart rate monitor sensor 815. The processor 450 can determine a third heart rate prediction range 855 of the flat-surface walking or running using the flat-surface walking or running machine model 835 and the current heartbeat data obtained by the heart rate monitor sensor 815. The processor 450 can determine a fourth heart rate prediction range 857 of the slope walking or running using the slope walking or running machine model 837 and the current heartbeat data obtained by the heart rate monitor sensor 815. The first heart rate prediction range 851 through the fourth heart rate prediction range 857 can have different predicted heartbeat data values.

Figure 9:
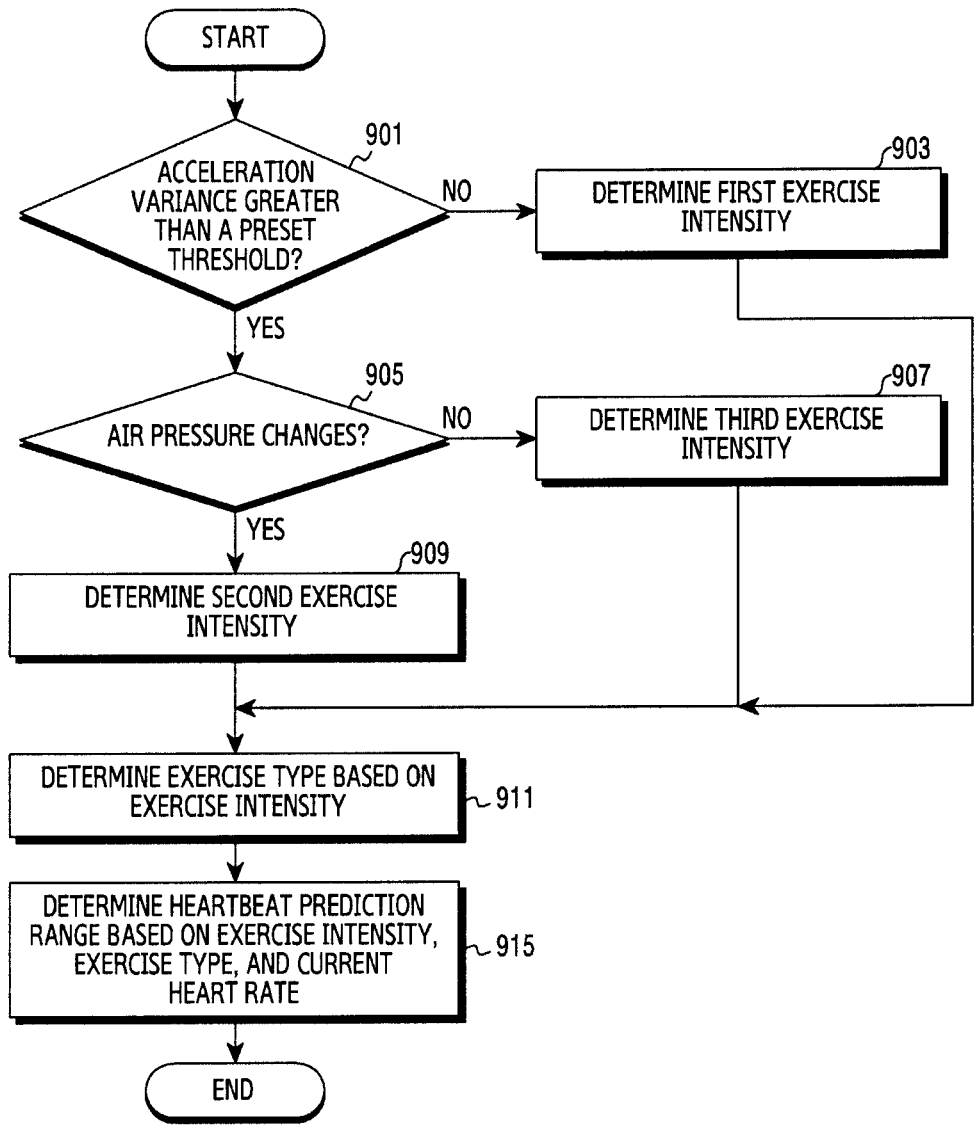
FIG. 9 is a flowchart of a method for determining a heartbeat prediction range in an electronic device according to various embodiments.

FIG. 9 is a flowchart of a method for determining a heartbeat prediction range in an electronic device according to various embodiments.

Referring to FIG. 9, in operation 901, the electronic device 400 (e.g., the processor 450) can determine whether acceleration variance is greater than a predetermined threshold or not. Motion sensor data (e.g., first motion sensor data) obtained from the sensor module 410 for a first duration can be acceleration data. For example, the acceleration data can be motion sensor data obtained from the motion sensor 413. Also, the processor 450 can obtain air pressure data from the air pressure sensor 415. The processor 450 can calculate variance of the acceleration data in the obtained motion sensor data.

For example, acceleration variance of the flat-surface running can be greater than acceleration variance of the flat-surface walking. Alternatively, acceleration variance of the elliptical training can be smaller than variance of the rowing machine. The processor 450 can define a threshold for determining whether the acceleration variance is considerable or not. For example, the threshold can be greater than the acceleration variance of the walking and smaller than the acceleration variance of the running. Alternatively, the threshold can be greater than the acceleration variance of the elliptical training and smaller than the acceleration variance of the rowing machine. The threshold can be set by the electronic device 400 or the user.

The processor 450 can determine the "great" acceleration variance when the acceleration variance exceeds a preset threshold, and determine the "small" acceleration variance when the acceleration variance falls below the same or a different threshold. The processor 450 can perform operation 905 for the considerable acceleration variance, and perform operation 903 for the small acceleration variance.

When the acceleration variance is not considerable, the electronic device 400 (e.g., the processor 450) can determine a first exercise intensity in operation 903. The processor 450 can determine an exercise intensity based on a user motion in a first duration, as the first exercise intensity. According to various embodiments, the processor 450 can divide the exercise intensity into various levels such as three levels, five levels, or ten levels. Hereafter, while the exercise intensity includes three levels to ease the understanding, the exercise intensity is not limited to those. For example, the processor 450 can divide the exercise intensity into three levels of high, moderate, and low. The first exercise intensity corresponds to the low exercise intensity, which is the lowest exercise intensity.

When the acceleration variance is detected as "great" (e.g., greater than the relevant threshold), the electronic device 400 (e.g., the processor 450) can whether the air pressure changes in operation 905. The processor 450 can determine variance of the air pressure data obtained by the air pressure data 415 in the first duration. The air pressure data can be detected when the user climbs or descends a slope such as hiking or stairs. Although the air pressure data is detected, a smooth slope may not heavily affect the exercise intensity and thus the processor 450 can determine a slope threshold by considering the effect of the slope on the exercise. For example, the slope threshold can be set by the electronic device 400 or the user.

When the air pressure data exceeds the slope threshold, the processor 450 can determine variance of the air pressure data. When the air pressure data falls below the slope threshold, the processor 450 can determine no variance of the air pressure data. With the variance of the air pressure data, the processor 450 can conduct operation 909. Without the variance of the air pressure data, the processor 450 can conduct operation 907.

Without the variance of the air pressure data, the electronic device 400 (e.g., the processor 450) can determine a third exercise intensity in operation 907. The processor 450 can determine the exercise intensity of the user motion in the first duration, as the third exercise intensity. The third exercise intensity corresponds to the high exercise intensity, which is the highest exercise intensity.

With the variance of the air pressure data, the electronic device 400 (e.g., the processor 450) can determine a second exercise intensity in operation 909. The processor 450 can determine the exercise intensity of the user motion in the first duration, as the second exercise intensity. The second exercise intensity corresponds to the moderate exercise intensity, which is the medium exercise intensity.

According to various embodiments, without the variance of the air pressure data, the processor 450 can determine the second exercise intensity. With the variance of the air pressure data, the processor 450 can determine the third exercise intensity. For example, uphill walking/running can have relatively smaller acceleration variance than the flat-surface walking/running and a higher exercise intensity than the flat-surface walking/running though the acceleration reduces as the air pressure changes considerably. Conversely, downhill walking/running can have relatively greater acceleration variance than the flat-surface walking/running and a faster speed as the air pressure changes greatly, but currently the acceleration variance can rapidly increase. When the air pressure changes greatly, the processor 450 can lower a weight which reflects the acceleration variance on the exercise intensity. In this case, the exercise intensity can increase slightly even when the acceleration variance increases severely.

According to various embodiments, the processor 450 can adjust the weight which reflects the acceleration variance on the exercise intensity, based on the air pressure change. For example, when detecting the air pressure data, the processor 450 can lower the weight which reflects the acceleration variance on the exercise intensity. With no variance of the air pressure data (e.g., the flat-surfing walking or running), the processor 450 can increase the weight which reflects the acceleration variance on the exercise intensity.

In operation 911, the electronic device 400 (e.g., the processor 450) can determine an exercise type based on the exercise intensity. For example, the exercise type corresponding to the first exercise type can include the walking or elliptical exercise. The exercise type corresponding to the second exercise type can include the uphill walking/running or the downhill walking/running. The exercise type corresponding to the third exercise type can include the running or the rowing machine.

In operation 915, the electronic device 400 (e.g., the processor 450) can determine a heartbeat prediction range based on at least one of the exercise intensity, the exercise type, and a current heart rate. The current heart rate can indicate the first heartbeat data acquired in the first duration. For example, the processor 450 can set an exercise coefficient based on the exercise intensity and the exercise type, and calculate predicted heartbeat data using the exercise coefficient and the current heart rate. The processor 450 can calculate the predicted heartbeat data based on Equation 5.

$$HR_{Pred} = HR_{Cur} \times (1 + C_{Exer}) \qquad (5)$$

$HR_{Pred}$: predicted HR
$HR_{Cur}$: current HR
$C_{Exer}$: exercise coefficient The processor 450 can determine the heartbeat prediction range by taking into account a margin of error based on the predicted heartbeat data. For example, when the predicted heartbeat data is 120 based on Equation 5, the processor 450 can determine the heartbeat prediction range to 110~130 based on the margin of error of ±7.

According to various embodiments, the processor 450 can set different margins of error according to the predicted heartbeat data. For example, when the predicted heartbeat data is 100, the margin of error can be set to ±10. When the predicted heartbeat data is 120, the margin of error can be set to ±7. When the predicted heartbeat data is 140, the margin of error can be set to ±5. The processor 450 may set different margins of error by considering at least one of the exercise intensity, the exercise type, and the current heart rate.

According to various embodiments, the processor 450 can determine the heartbeat prediction range by further considering user's body information. For example, the user's body information can include at least one of a height, a weight, an age, a gender, a resting heart rate, a maximum heart rate based on the age, a blood pressure, body fat, and blood type. The blood pressure can differ according to the age or the gender, and the blood pressure can affect the heartbeat data. The maximum heart rate can be determined based on the age. Hence, the processor 450 can determine an accurate heartbeat prediction range by further considering the user body information together with the exercise intensity, the exercise type, and the current heart rate.

According to various embodiments, the processor 450 may set different margins of error of the predicted heartbeat data by taking into account the user's body information. For example, the processor 450 can widen the margin of error (e.g., ±15) for a high blood pressure, and narrow the margin of error (e.g., ±5) for a low blood pressure. The processor 450 may set different margins of error by further considering at least one of the exercise intensity, the exercise type, the current heart rate, and the user body information.

Figure 10:
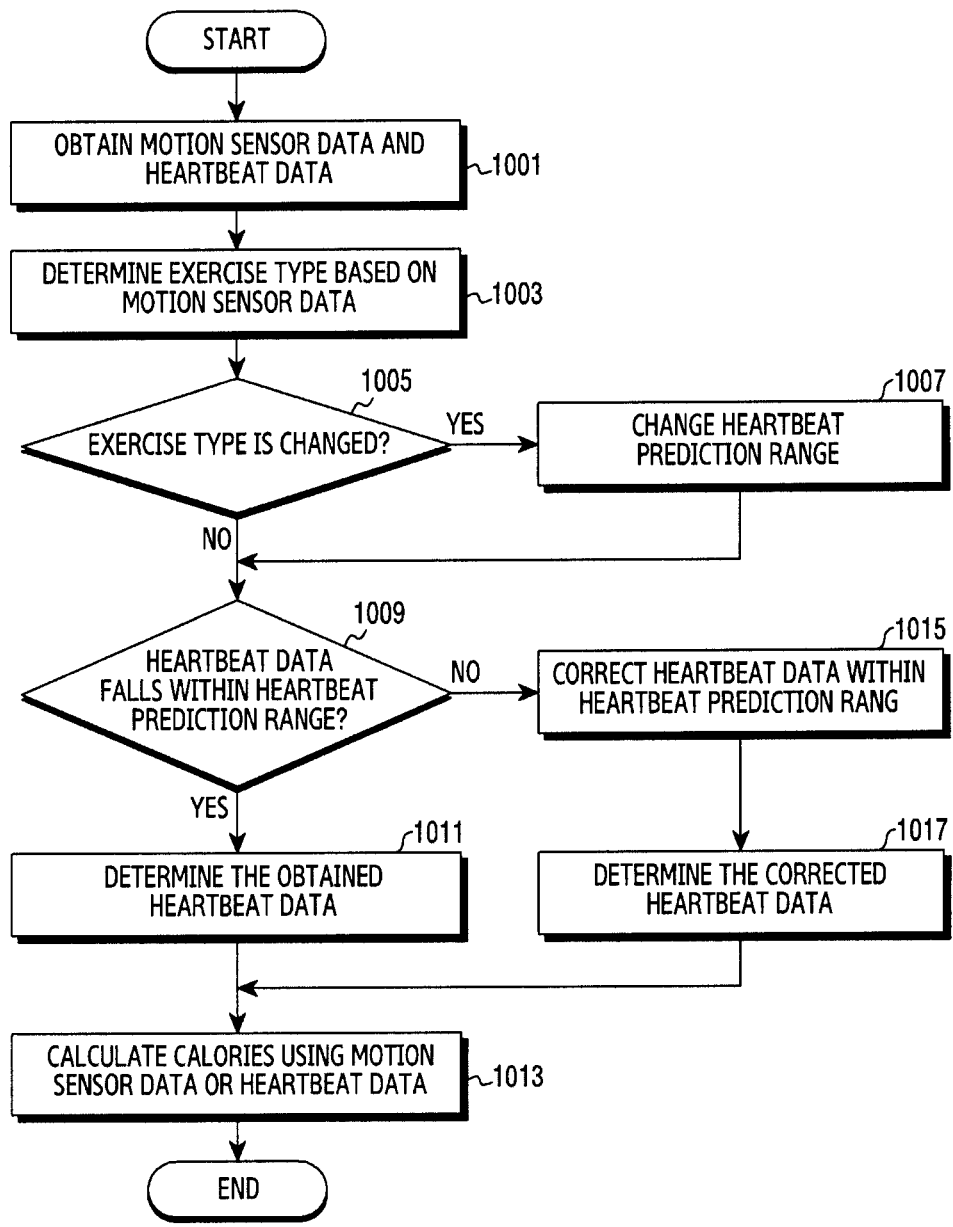
FIG. 10 is a flowchart of a method for providing information using heartbeat data of an electronic device according to various embodiments.

FIG. 10 is a flowchart of a method for providing information using heartbeat data of an electronic device according to various embodiments.

Referring to FIG. 10, in operation 1001, the electronic device 400 (e.g., the processor 450) can obtain motion sensor data and heartbeat data. The processor 450 can obtain the motion sensor data from the motion sensor 413 for a certain duration (e.g., a second duration) or at a time point in the second duration. Also, the processor 450 can obtain air pressure data from the air pressure sensor 415. The heartbeat data can be sensor data obtained from the heart rate monitor sensor 411 in the certain duration (e.g., the second duration). That is, the motion sensor data and the heartbeat data can be acquired after an exercise type is determined using previous sensor data. Referring back to FIG. 5, the motion sensor data and the heartbeat data obtained in operation 1001 can indicate the second motion sensor data and the second heartbeat data acquired in the second duration (e.g., in operation 507).

In operation 1003, the electronic device 400 (e.g., the processor 450) can determine the exercise type based on the motion sensor data. For example, for great acceleration variance, the processor 450 can determine the moderate exercise intensity and the exercise type as the running or the rowing machine. For small acceleration variance, the processor 450 can determine the low exercise intensity and the exercise type as the walking or the elliptical exercise. Also, the processor 450 can determine the exercise type based on the motion sensor data and the air pressure data. For example, when the acceleration variance is great and an air pressure variance is great, the processor 450 can determine the moderate exercise intensity and the exercise type as the climbing (e.g., downhill walking or running). When the acceleration variance is small and the air pressure variance is small, the processor 450 can determine the high exercise intensity and the exercise type as the climbing (e.g., uphill walking or running).

In operation 1005, the electronic device 400 (e.g., the processor 450) can determine whether the exercise type has changed. That is, user may be walking on level ground, an uphill incline, or a downhill incline. Despite executing the same walking exercise, the predicted heart rate or the consumed calories can vary according to an exercise intensity which changes with the slope. Accordingly, as the sensed data changes, the processor 450 can determine whether a current exercise type has changed from a previous one other, and alter configuration to ensure acquisition of more accurate heartbeat data.

When the exercise type is changed, the processor 450 can perform operation 1007. When the exercise type is not changed, the processor 450 can perform operation 1009.

When the exercise type is changed, the processor 450 (e.g., the processor 450) can change a heartbeat prediction range in operation 1007. The heartbeat prediction range can predict next heartbeat data based on the current exercise intensity, the current exercise type, and the current heartbeat data. However, since the current exercise can be different from the next exercise in type, when the exercise type changes, the processor 450 may modify the heartbeat prediction range to ensure a more accurate prediction. The processor 450 can change predicted heartbeat data based on the changed exercise intensity and the changed exercise type.

In operation 1009, the electronic device 400 (the processor 450) can determine whether the heartbeat data falls within the heartbeat prediction range. For example, when the heartbeat prediction range is not changed, the processor 450 can determine whether the heartbeat data obtained in operation 1001 falls within the original heartbeat prediction range. Alternatively, when the heartbeat prediction range is changed, the processor 450 can determine whether the heartbeat data obtained in operation 1001 is included in the modified heartbeat prediction range.

When the heartbeat data falls within the heartbeat prediction range, the processor 450 can conduct operation 1011. When the heartbeat data does not fall within the heartbeat prediction range, the processor 450 can conduct operation 1015.

When the heartbeat data falls within the heartbeat prediction range, the electronic device 300 (e.g., the processor 450) can determine the obtained heartbeat data as data for the measurement in operation 1011.

In operation 1013, the electronic device 400 (e.g., the processor 450) can calculate calories using the motion sensor data or the heartbeat data. For example, using the heartbeat data obtained in operation 1001, the processor 450 can calculate calories consumed by a user's motion for a certain duration (e.g., a second duration). The processor 450 can calculate the calories using the heartbeat data obtained in operation 1001 based on the exercise type, or calculate the calories using the motion sensor data and the heartbeat data acquired in operation 1001. The processor 450 can provide a user interface regarding at least one of the motion sensor data, the heartbeat data, and the calories.

When the heartbeat data does not fall within the heartbeat prediction range, the electronic device 400 (e.g., the processor 450) can correct the heartbeat data within the heartbeat prediction range in operation 1015. The processor 450 can rely more on the predicted heartbeat data than the heartbeat data obtained in operation 1001. When the heartbeat data does not fall within the heartbeat prediction range, the processor 450 can correct the heartbeat data with other heartbeat data of the heartbeat prediction range. The corrected heartbeat data can be included in the heartbeat prediction range.

According to various embodiments, the processor 450 can correct the heartbeat based on a maximum value and a minimum value of the heartbeat prediction range, and the heartbeat data (e.g., the heartbeat data acquired by the heart rate monitor sensor). Alternatively, the processor 450 can determine at least one of the maximum value, the minimum value, and an average value of the heartbeat prediction range, as the predicted heartbeat data. For example, when the predicted heartbeat data is 120, the heartbeat prediction range can be 110~130, the minimum value of the heartbeat prediction range can be 110, and the maximum value of the heartbeat prediction range can be 130. When the heartbeat data is 105, a difference value (e.g., 5) between the minimum value and the heartbeat data is smaller than a difference value (e.g., 10) between the predicted heartbeat data and the minimum value and thus the processor 450 can correct the heartbeat data close to the minimum value. For example, the processor 450 can correct the heartbeat data to the value 115 between the predicted heartbeat data and the minimum value.

Alternatively, when the heartbeat data is 100, the difference value (e.g., 10) between the minimum value and the heartbeat data is equal to the difference value (e.g., 10) between the predicted heartbeat data and the minimum value and thus the processor 450 can correct the heartbeat data with the minimum value. For example, the processor 450 can correct the heartbeat data to the minimum value 110 of the predicted heartbeat range. Alternatively, when the heartbeat data is 135, the difference value (e.g., 5) between the maximum value and the heartbeat data is smaller than the difference value (e.g., 10) between the predicted heartbeat data and the maximum value and thus the processor 450 can correct the heartbeat data close to the maximum value. For example, the processor 450 can correct the heartbeat data to the value 125 between the predicted heartbeat data and the maximum value.

Alternatively, when the heartbeat data is 140, the difference value (e.g., 10) between the maximum value and the heartbeat data is equal to the difference value (e.g., 10) between the predicted heartbeat data and the maximum value and thus the processor 450 can correct the heartbeat data with the maximum value. For example, the processor 450 can correct the heartbeat data to the maximum value 130 of the predicted heartbeat range. Alternatively, the processor 450 may correct the heartbeat data with the predicted heartbeat data by taking into account the exercise intensity, the exercise type, and the heartbeat data. In this case, the processor 450 can correct the heartbeat data with 120.

In operation 1017, the electronic device 400 (e.g., the processor 450) can determine the corrected heartbeat data as data for the measurement. Next, the processor 450 can calculate the calories using the motion sensor data or the corrected heartbeat data in operation 1013.

According to various embodiments, a method for operating an electronic device which includes a motion sensor 413 and a heart rate monitor sensor 411, can include obtaining first motion sensor data for a first duration using the motion sensor 413, and obtaining first heartbeat data for the first duration using the heart rate monitor sensor 411, determining an exercise type based on the first motion sensor data, determining a heartbeat prediction range based on at least one of the first motion sensor data, the exercise type, and the first heartbeat data, determining whether second heartbeat data obtained for a second duration falls within the heartbeat prediction range, and determining heartbeat data of the second duration based on the determination result.

Determining whether the second heartbeat data falls within the heartbeat prediction range can include, when the second heartbeat data falls within the heartbeat prediction range, determining the second heartbeat data as the heartbeat data of the second duration, and, when the second heartbeat data does not fall within the heartbeat prediction range, determining third heartbeat data in the heartbeat prediction range as the heartbeat data of the second duration.

Determining the third heartbeat data can include determining the third heartbeat data to at least one of a maximum value, a minimum value, and an average value of the heartbeat prediction range.

The method can further include, when the second heartbeat data falls within the heartbeat prediction range, calculating calories using the second motion sensor data or the second heartbeat data obtained in the second duration, when the second heartbeat data does not fall within the heartbeat prediction range, calculating calories using the second motion sensor data obtained in the second duration or the third heartbeat data within the heartbeat prediction range.

The method can further include determining an exercise intensity or the exercise type based on the first motion sensor data, determining predicted heartbeat data based on at least one of the exercise intensity, the exercise type, and the first heartbeat data, and determining the heartbeat prediction range by considering a margin of error based on the predicted heartbeat data.

The first motion sensor data can include acceleration data, and determining the exercise intensity or the exercise type can include determining the exercise intensity or the exercise type according to acceleration variance based on the acceleration data or variance of air pressure data using an air pressure sensor 415.

According to various embodiments, a computer-readable recording medium can include a program for obtaining first motion sensor data for a first duration using the motion sensor, and obtaining first heartbeat data for the first duration using the heart rate monitor sensor, determining an exercise type based on the first motion sensor data, determining a heartbeat prediction range based on at least one of the first motion sensor data, the exercise type, and the first heartbeat data, determining whether second heartbeat data obtained for a second duration falls within the heartbeat prediction range, and determining heartbeat data of the second duration based on the determination result.

The computer-readable recording medium can include a hard disk, a floppy disk, magnetic media (e.g., a magnetic tape), optical media (e.g., a Compact Disc (CD)-Read Only Memory (ROM), a DVD), magneto-optical media (e.g., a floptical disk), and an internal memory. An instruction can include machine code made by a compiler or code executable by an interpreter. A module or a program module according to various embodiments can include at least one or more of the aforementioned components, omit some of them, or further include additional other components. Operations performed by a module, a program module, or other components according to various embodiments can be executed in a sequential, parallel, repetitive, or heuristic manner. At least some operations can be executed in a different order or be omitted, or other operations can be added.

The control unit or processor may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. In addition, an artisan understands and appreciates that a "processor" or "microprocessor" may be hardware in the claimed disclosure.

While the disclosure has been shown and described with reference to certain example embodiments thereof, it will be understood by those skilled in the art that various changes in form and details may be made therein without departing from the disclosure as defined by the appended claims and their equivalents.

What is claimed is:
1. An electronic device comprising:
   a barometer sensor,
   a motion sensor;
   a heart rate monitor sensor; and
   a processor functionally coupled with the motion sensor and the heart rate monitor sensor, wherein the processor is configured to:
      obtain first motion sensor data for a first duration using the motion sensor, obtain first heartbeat data for the first duration using the heart rate monitor sensor, and obtain air pressure data for the first duration using the barometer sensor, wherein the air pressure data indicates a variance in air pressure,
      determine an exercise type, based on the first motion sensor data and the air pressure data,
      lower a weight of the first motion sensor data reflected in the determination of the exercise type, when the variance in the air pressure data is greater than a threshold, determine a heartbeat prediction range based on at least one of the first motion sensor data, the exercise type, and the first heartbeat data, obtain second heartbeat data for a second duration using the heart rate monitor sensor, determine whether the second heartbeat data falls within the heartbeat prediction range, and determine whether to correct the second heartbeat data of the second duration based on the determination result of whether the second heartbeat data falls within the heartbeat prediction range.

2. The electronic device of claim 1, wherein the processor is further configured to determine the second heartbeat data as the heartbeat data of the second duration when the second heartbeat data is disposed within the heartbeat prediction range, and determine third heartbeat data in the heartbeat prediction range as the heartbeat data of the second duration when the second heartbeat data is disposed outside the heartbeat prediction range.

3. The electronic device of claim 2, wherein, when the second heartbeat data is disposed outside the heartbeat prediction range, the processor is further configured to:
determine the third heartbeat data based on a maximum value and a minimum value of the heartbeat prediction range, and the second heartbeat data, and corrects the second heartbeat data with the third heartbeat data.

4. The electronic device of claim 2, wherein the processor is further configured to determine at least one of the maximum value, the minimum value, and an average value of the heartbeat prediction range, as the third heartbeat data.

5. The electronic device of claim 2, wherein:
when the second heartbeat data is disposed within the heartbeat prediction range, the processor is further configured to calculate caloric consumption using a second motion sensor data or the second heartbeat data obtained in the second duration, and when the second heartbeat is disposed outside the heartbeat prediction range, the processor further configured to calculate caloric consumption using at least one of the second motion sensor data, and the third heartbeat data.

6. The electronic device of claim 1, wherein the processor further configured to calculate caloric consumption using the detected exercise type and the first heartbeat data, or using the detected exercise type, the first motion sensor data and the first heartbeat data.

7. The electronic device of claim 1, wherein the processor is further configured to:
determine an exercise intensity based on the first motion sensor data, determine predicted heartbeat data based on at least one of the exercise intensity, the exercise type, and the first heartbeat data, and determine the heartbeat prediction range by considering a margin of error based on the predicted heartbeat data.

8. The electronic device of claim 7, wherein the first motion sensor data further comprises acceleration data, and the processor is further configured to detect the exercise intensity or the exercise type according to an acceleration variance detected using at least one of the acceleration data, and the air pressure data retrieved using the barometer sensor.

9. The electronic device of claim 8, wherein, when the air pressure data indicates an absence or variance in air pressure, the processor is further configured to determine the predicted heartbeat data corresponding to changes in the acceleration variance.

10. The electronic device of claim 7, wherein the processor is further configured to set a particular margin of error from among a plurality of margins of error based on pre-association with a heart rate indicated by the predicted heartbeat data.

11. The electronic device of claim 1, wherein the processor is further configured to determine the heartbeat prediction range based on user body information.

12. The electronic device of claim 1, wherein the processor is further configured to: calculate a first quantity of calories consumed during the first duration using at least one of the first motion sensor data and the first heartbeat data, and control a display to display a user interface including at least one of the first motion sensor data, the first heartbeat data, and the first quantity of calories.

13. The electronic device of claim 1, wherein the processor comprises a first processor and a second processor, in which the first processor is activated while the electronic device is activated, and the second processor is selectively activated while the electronic device is activated.

14. The electronic device of claim 1, wherein the electronic device includes an attachment means to secure the electronic device to a user's body.

15. A method for operating an electronic device which comprises a barometer sensor, a motion sensor and a heart rate monitor sensor, the method comprising:
obtaining first motion sensor data for a first duration using the motion sensor, obtaining first heartbeat data for the first duration using the heart rate monitor sensor, and obtaining air pressure data for the first duration using the barometer sensor, wherein the air pressure data indicates a variance in air pressure;

determining an exercise type based on the first motion sensor data and the air pressure data;

lowering a weight of the first motion sensor data reflected in the determination of the exercise type, when the variance in the air pressure data is greater than a threshold;

determining a heartbeat prediction range based on at least one of the first motion sensor data, the exercise type, and the first heartbeat data;

determining whether second heartbeat data obtained for a second duration falls within the heartbeat prediction range; and determining whether to correct the second heartbeat data of the second duration based on the determination result of whether the second heartbeat data falls within the heartbeat prediction range.

16. The method of claim 15, wherein determining whether the second heartbeat data falls within the heartbeat prediction range comprises:
when the second heartbeat data is disposed within the heartbeat prediction range, determining the second heartbeat data as the heartbeat data of the second duration; and when the second heartbeat data is disposed outside the heartbeat prediction range, determining third heartbeat data in the heartbeat prediction range as the heartbeat data of the second duration.

17. The method of claim 16, wherein determining the third heartbeat data comprises:
determining the third heartbeat data to at least one of a maximum value, a minimum value, and an average value of the heartbeat prediction range.

18. The method of claim 16, wherein:
when the second heartbeat data is disposed within the heartbeat prediction range, caloric consumption is calculated using a second motion sensor data or the second heartbeat data obtained in the second duration, and
when the second heartbeat is disposed outside the heartbeat prediction range, caloric consumption is calculated using at least one of the second motion sensor data, and the third heartbeat data.

19. The method of claim 15, further comprising:
determining an exercise intensity based on the first motion sensor data;
determining predicted heartbeat data based on at least one of the exercise intensity, the detected exercise type, and the first heartbeat data; and
wherein the heartbeat prediction range is generated using a margin of error based on the predicted heartbeat data.

* * * * *